US008101196B2

(12) United States Patent
Luthra et al.

(10) Patent No.: US 8,101,196 B2

(45) Date of Patent: Jan. 24, 2012

(54) POLYSACCHARIDE BIOMATERIALS AND METHODS OF USE THEREOF

(75) Inventors: Ajay K. Luthra, Middlesex (GB); Shivpal S. Sandhu, Slough (GB); John O. Hudson, Leicester (GB)

(73) Assignee: BioInteractions, Ltd., Reading (GB)

( * ) Notice: Subject to any disclaimer, the term of this patent is extended or adjusted under 35 U.S.C. 154(b) by 644 days.

(21) Appl. No.: 10/179,453

(22) Filed: Jun. 25, 2002

(65) Prior Publication Data

US 2003/0021762 A1 Jan. 30, 2003

Related U.S. Application Data

(60) Provisional application No. 60/301,176, filed on Jun. 26, 2001.

(51) Int. Cl.

*A61F 2/82* (2006.01)
*A61K 31/715* (2006.01)
*A61K 38/14* (2006.01)
*A61K 47/30* (2006.01)

(52) U.S. Cl. ........ 424/422; 424/423; 424/424; 424/425; 514/20.9; 514/54; 514/56; 514/62; 514/772.3; 514/772.4; 514/822; 514/944; 514/953

(58) Field of Classification Search .................. 424/423, 424/78.17, 78.18; 604/266, 508, 2.66
See application file for complete search history.

(56) References Cited

U.S. PATENT DOCUMENTS

| | | | | |
|---|---|---|---|---|
| 3,954,583 A | | 5/1976 | Lednicer et al. | |
| 4,082,727 A | | 4/1978 | Nagata et al. | 260/46.5 |
| 4,239,664 A | | 12/1980 | Teng et al. | 260/17.4 |
| 4,331,697 A | | 5/1982 | Kudo et al. | 427/2 |
| 4,469,827 A | | 9/1984 | Pusineri et al. | 524/27 |
| 4,722,906 A | | 2/1988 | Guire | |
| 4,987,181 A | | 1/1991 | Bichon et al. | 525/54.1 |
| 5,047,020 A | | 9/1991 | Hsu | 604/266 |
| 5,183,872 A | | 2/1993 | Heidel et al. | 527/300 |
| 5,270,046 A | * | 12/1993 | Sakamoto et al. | 424/422 |
| 5,344,455 A | | 9/1994 | Keogh et al. | 623/11 |
| 5,410,016 A | | 4/1995 | Hubbell et al. | |
| 5,417,969 A | | 5/1995 | Hsu et al. | 424/78.27 |
| 5,462,976 A | | 10/1995 | Matsuda et al. | 522/74 |
| 5,512,329 A | | 4/1996 | Guire et al. | 427/508 |
| 5,541,167 A | | 7/1996 | Hsu et al. | 514/56 |
| 5,583,213 A | * | 12/1996 | Yafuso et al. | 536/55.3 |
| 5,728,751 A | | 3/1998 | Patnaik | 523/112 |
| 5,741,551 A | | 4/1998 | Guire et al. | 427/407.1 |
| 5,741,881 A | | 4/1998 | Patnaik | 528/75 |
| 5,763,504 A | | 6/1998 | Matsuda et al. | 522/87 |
| 5,776,184 A | | 7/1998 | Tuch | 623/1 |
| 5,783,570 A | | 7/1998 | Yokota et al. | 514/56 |
| 5,834,274 A | | 11/1998 | Hubbell et al. | |
| 5,837,747 A | | 11/1998 | Soon-Shiong et al. | 522/26 |
| 5,846,530 A | | 12/1998 | Soon-Shiong et al. | 424/93.7 |
| 5,851,229 A | | 12/1998 | Lentz et al. | |
| 5,855,618 A | | 1/1999 | Patnaik et al. | 623/11 |
| 5,873,906 A | * | 2/1999 | Lau et al. | 128/898 |
| 5,877,263 A | | 3/1999 | Patnaik et al. | 525/453 |
| 5,945,457 A | | 8/1999 | Plate et al. | 514/772.1 |
| 5,993,890 A | | 11/1999 | Marchant et al. | 427/2.3 |
| 6,007,833 A | | 12/1999 | Chudzik et al. | |
| 6,027,741 A | | 2/2000 | Cialdi et al. | |
| 6,059,823 A | * | 5/2000 | Holman et al. | 623/1.15 |
| 6,060,582 A | | 5/2000 | Hubbell et al. | 528/354 |
| 6,096,798 A | | 8/2000 | Luthra et al. | 523/105 |
| 6,121,027 A | | 9/2000 | Clapper et al. | 435/180 |
| 6,127,348 A | | 10/2000 | Roufa et al. | 514/59 |
| 6,248,127 B1 | * | 6/2001 | Shah et al. | 623/1.15 |
| 6,258,121 B1 | * | 7/2001 | Yang et al. | 623/1.46 |
| 6,358,557 B1 | * | 3/2002 | Wang et al. | 427/2.24 |
| 6,368,356 B1 | * | 4/2002 | Zhong et al. | 623/23.75 |
| 6,514,734 B1 | | 2/2003 | Clapper et al. | |
| 6,630,460 B2 | * | 10/2003 | Koulik | 514/56 |
| 2001/0056301 A1 | * | 12/2001 | Goupil et al. | 623/11.11 |

FOREIGN PATENT DOCUMENTS

| | | |
|---|---|---|
| EP | 049828 A1 | 10/1981 |
| EP | 049828 B1 | 10/1981 |
| EP | 0149693 | 7/1985 |
| EP | 0769503 | 10/1995 |
| EP | 0781566 | 12/1996 |
| SU | 1078894 | 1/1998 |
| WO | WO 90/00887 | 2/1990 |
| WO | WO 97/01173 | 1/1997 |
| WO | WO 97/30092 | 8/1997 |
| WO | WO 97/41164 | 11/1997 |
| WO | WO 00/12146 | 3/2000 |

OTHER PUBLICATIONS

ScienceDaily, "Solubility" [online], [retrieved on Mar. 8, 2010], retrieved from the internet: <URL:http://www.sciencedaily.com/artilces/s/solubility.htm>.*

Ratner et al., *Biomaterials Science, An Introduction to Materials in Medicine*, 1996 Academic Press, pp. 60-64, 165-173, and 193-199.

European Search Report (PCT/GB02/02940), (2003).

(Continued)

*Primary Examiner* — Johann Richter
*Assistant Examiner* — Frank Choi
(74) *Attorney, Agent, or Firm* — Dardi & Herbert, PLLC

(57) ABSTRACT

The invention includes a medical hydrogel made from polymerized polysaccharide macromers. The macromers are preferably polysaccharides decorated with polymerizable groups, for example, methacrylates. The macromers may also be made into polymers of at least two macromers polymerized together. These polymers are preferably multi-armed or high-molecular weight and used for medical uses, for example, making coatings on medical devices. Macromers of N-vinylpyrrolidone are also disclosed herein.

50 Claims, 8 Drawing Sheets

OTHER PUBLICATIONS

Derwent Publications Ltd., London, GB; AN 1998-493796 [42] XP 002217699, (1998).

Handbook of Pharmaceutical Excipients (Kibbe, eds.), p. 163-164, (2000).

* cited by examiner 10
14
16
12

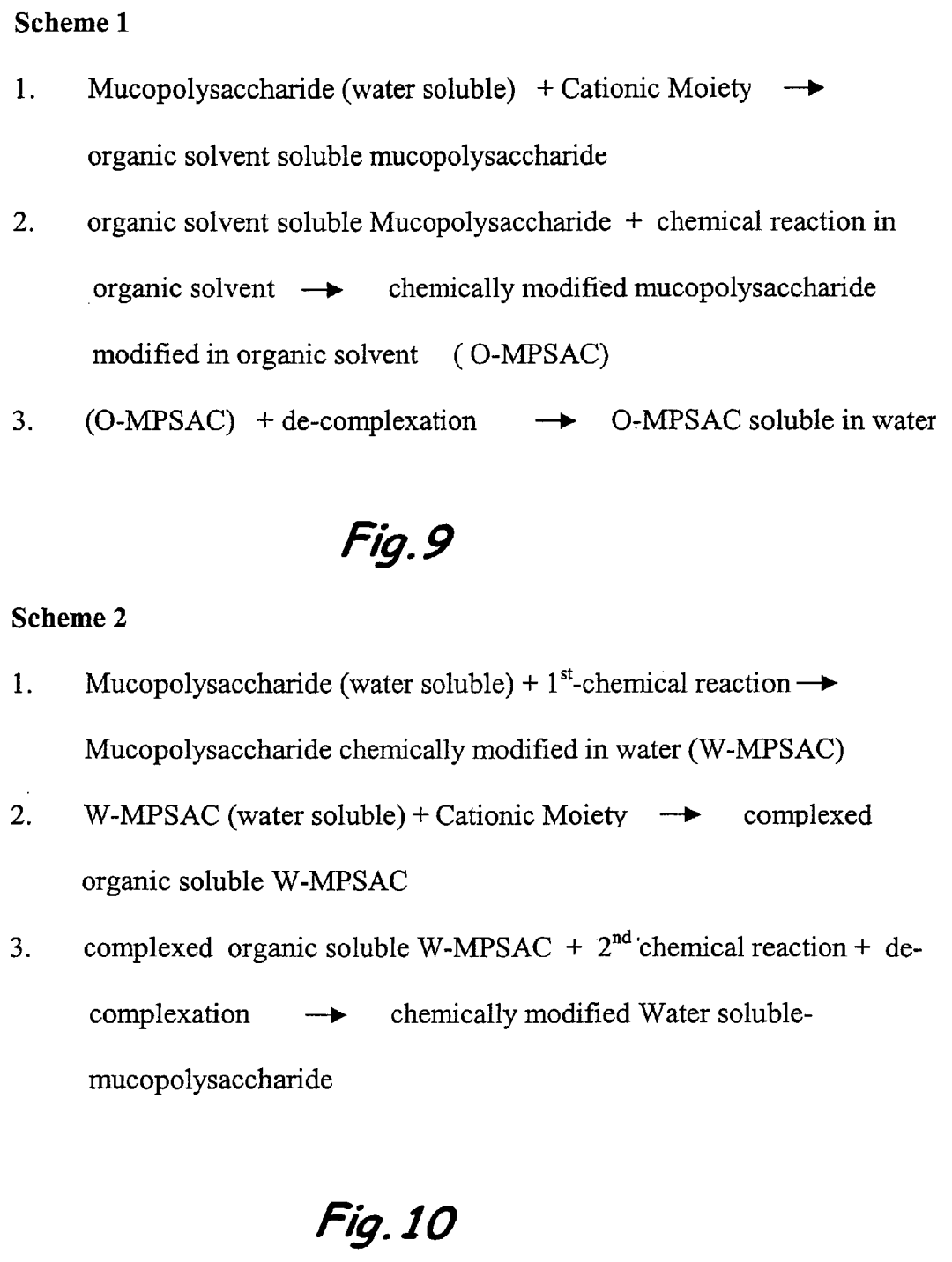

Scheme 1

1. Mucopolysaccharide (water soluble) + Cationic Moiety → organic solvent soluble mucopolysaccharide
2. organic solvent soluble Mucopolysaccharide + chemical reaction in organic solvent → chemically modified mucopolysaccharide modified in organic solvent ( O-MPSAC)
3. (O-MPSAC) + de-complexation → O-MPSAC soluble in water

*Fig. 9*

Scheme 2

1. Mucopolysaccharide (water soluble) + 1st-chemical reaction → Mucopolysaccharide chemically modified in water (W-MPSAC)
2. W-MPSAC (water soluble) + Cationic Moiety → complexed organic soluble W-MPSAC
3. complexed organic soluble W-MPSAC + 2nd chemical reaction + de-complexation → chemically modified Water soluble-mucopolysaccharide

*Fig. 10*

POLYSACCHARIDE BIOMATERIALS AND METHODS OF USE THEREOF

RELATED APPLICATIONS

The present application claims priority to U.S. provisional patent application Ser. No. 60/301,176, entitled "Polysaccharide Biomaterials and Methods of Use Thereof", filed Jun. 26, 2001, which is hereby incorporated herein by reference.

FIELD OF INVENTION

The invention relates to body treating compositions, especially those formed as a matrix. More specifically, the invention includes hydrogel matrices of polymerized polysaccharides, especially heparin, so as to create a hydrogel, especially for vascular graft applications.

BACKGROUND OF THE INVENTION

Many synthetic materials have been medically used in the body, including polyester (e.g., DACRON™), polyethylene (e.g., milk jugs), and fluorocarbons (e.g., TEFLON™), and metals. A patient's body responds by treating a synthetic material as an invader, although it responds only mildly in some medical applications; for example, a metal hip implant is generally well tolerated. One common response to an implant is called a foreign body response in which the body forms a capsule of cells around the material; the body's response to a splinter is a foreign body response. When synthetic material is used as an artificial blood vessel, for example, the blood that flows through the artificial blood vessel reacts with the synthetic material. The reaction can cause clots to form that flow downstream that may eventually become stuck in a smaller vessel; if this happens in the brain, it is called a stroke. The blood clot can also grow on the inside of the vessel and block or severely restrict the blood flow. Blood's clotting mechanism is highly reactive and, despite years of medical research, no implantable blood-contacting synthetic material has yet been found that does not cause blood to react.

Tubes made of polyester or fluorocarbons are currently used as large diameter blood vessels. The blood clots onto the interior walls and reduces the inside diameter of the vessel but the blood flow is not unduly reduced. The blood clot on the tubular wall serves as a protective layer that elicits very little reaction from blood flowing through the vessel. This approach, however, does not work for small diameter blood vessels because the small diameter tubes are blocked when the blood clots onto the walls.

There are no currently known materials and techniques for manufacturing small diameter vascular grafts made of synthetic materials. Unfortunately, there is a great need for such grafts. One example is the condition called deep vein thrombosis wherein a patient's veins become blocked. The blood drains poorly from the leg and amputation can result. Unlike heart bypass surgeries where the patient often has some blood vessels that can be harvested from elsewhere in the body and sewn into place, there are few choices for replacing the long veins of the leg.

One area of synthetic biomaterials research has focused on hydrogels, materials that have a high water content and are soft and slippery. Soft contact lenses are examples of hydrogels. The materials used to make a pure hydrogel might all dissolve in water but the hydrogel itself does not dissolve in water because the materials are cross-linked; in other words, the individual molecular chains are linked together like the strands in a net or a spider's web. Hydrogels tend to elicit a milder foreign body response than other synthetic materials. Some hydrogel biomaterials that are currently considered to be commercially useful are made from polyethylene glycol (PEG), hyaluronic acid, and alginates. Although hydrogels tend to elicit less blood clotting than other synthetic materials, hydrogels have not previously been successfully used to make a small diameter vascular graft.

Scientists have also tried to use heparin to coat the inside of vascular grafts made of synthetic materials. Heparin is a molecule that belongs to a group of molecules called polysaccharides that are polymers made from combinations of sugar monomers. There are many sugars; glucose and sucrose (table sugar) are two examples. Polysaccharides are naturally-occurring polymers. Polymers are molecules built up by the repetition of smaller units that are sometimes called monomers. Polymers are typically made by special chemical schemes that make the monomers chemically react with each other to form molecular chains that can range in length from short to very long molecules. Polymers can be assembled into larger materials; for example, many polymers may be linked together to form a hydrogel.

Heparin is a polysaccharide polymer with an important property: it interferes with key molecules in the blood clotting mechanism such that the blood will not clot. Coating the inside of a synthetic material tube with heparin tends to increase the amount of time that the tube remains open to blood flow but, to date, small diameter vascular grafts coated with heparin have failed to resist blockage by blood clots for a medically useful length of time.

Heparin has been applied to materials in many ways. General strategies include letting it naturally stick to a surface (termed adsorption), making a charge-charge bond with the surface (e.g., an ionic bond), and attaching it via an even stronger, more permanent chemical linkage such as a covalent bond. Heparin has been applied as a thin coating of polymers adsorbed to a surface by dipping the surface into a solution of heparin or drying the heparin onto the surface. Heparin has a negative charge and has been exposed to surfaces that have a positive charge so that it remains there via a charge-charge interaction. Photoactivated chemical groups have been put onto heparin so that the heparin is put close to the surface, the surface is bathed in light, and the photoactive groups make permanent covalent chemical bonds between the heparin polymer and the surface. Similarly, heparin has been chemically attached to monomers that have then been reacted with the surface.

Patent families and patent applications that describe the use of heparin include U.S. Pat. No. 6,127,348, which include descriptions of cross-linked alginate and certain other polysaccharides as compositions useful for inhibiting fibrosis. U.S. Pat. No. 6,121,027 includes descriptions of decorating heparin with a photoactive cross linking chemical group. Application PCT GB9701173 and U.S. Pat. No. 6,096,798 include descriptions of heparins with monomers used to make polymers. U.S. Pat. Nos. 5,763,504 and 5,462,976 include descriptions of glycosaminoglycans derivatized with photoactive groups and cross-linked thereby. U.S. Pat. No. 6,060,582 includes descriptions of macromers with a water soluble region, a biodegradable region, and at least two free-radical polymerizable regions. Other patents include descriptions of a polysaccharide reacted with other polymers, decorated with a polymerizable group, and/or reacted to form a coating on a surface; including U.S. Pat. Nos. 5,993,890; 5,945,457; 5,877,263; 5,855,618; 5,846,530; 5,837,747; 5,783,570; 5,776,184; 5,763,504; 5,741,881; 5,741,551; 5,728,751;

5,583,213; 5,512,329; 5,462,976; 5,344,455; 5,183,872; 4,987,181; 4,331,697; 4,239,664; 4,082,727; and European patents 049,828 A1 & B1.

Despite many years of research in the areas of polysaccharides, hydrogels, and blood-contacting materials, the need for better implantable synthetic materials that cause little or no unfavorable reaction from a patient's body remains acute. In particular, there is a great need for a medically useful small diameter vascular graft made of synthetic materials.

SUMMARY OF THE INVENTION

The present invention meets all of these needs by providing embodiments that include synthetic materials that successfully combine the advantages of polysaccharides and hydrogels in a medically useful manner so that they may be used for devices, including small diameter vascular grafts. Other embodiments of the invention include hydrogels made of polysaccharides and materials and methods for making such hydrogels, as well as products that incorporate such hydrogels. One embodiment of the invention is a hydrogel made of a polysaccharide, for example heparin. Another embodiment is a hydrogel made by polymerizing heparin macromers. Another embodiment is a small diameter vascular graft made by polymerizing heparin macromers around a tube, for example a polyester tube.

An embodiment of the invention is a medical apparatus having polysaccharide macromers polymerized into a three-dimensional crosslinked hydrogel that makes a hollow cylinder; with the cylinder being formed during polymerization of the polysaccharide macromers. A hollow cylinder is essentially equivalent to a tubular structure and may be made out of any material, e.g., metals, plastics, ceramics, having a variety of properties, including e.g., rigid, compliant, and elastic.

Another embodiment of the invention is a biocompatible encapsulation for an inert medical device. The encapsulation has polysaccharide macromers polymerized into a three-dimensional crosslinked hydrogel that encapsulates the medical device.

Another embodiment of the invention is a medical apparatus made of a material that has a heparin macromers polymerized into a three-dimensional crosslinked hydrogel that forms a hollow cylinder that is not covalently bonded to another material.

Another embodiment of the invention is a pollyvinylpyrrolidone macromer. Another embodiment is a biocompatible coating system that has polyvinylpyrrolidone macromers polymerized into a three-dimensional crosslinked material that contacts a medical device and thereby forms the coating.

Another embodiment of the invention is a polysaccharide polymer of at least two polysaccharide macromers polymerized together. The polymer is preferably in an isolatable form. The macromers may have polymerizable moieties such as polyhydroxyethylmethylacrylates, methyl methacrylates, methacrylates, acrylates, photopolymerizable monomers, monomers with hydroxyl groups, monomers with glycerol groups, monomers with polyoxyalkylene ether groups, monomers with polypropylene oxide groups, monomers with vinyl groups, monomers with zwitterionic groups, monomers with silicone groups, monomers having sulphate groups, monomers having sulphonate groups, and heparin monomer.

Another embodiment of the invention is a method of making a medical apparatus from a material that includes a plurality of polysaccharide macromers by polymerizing the macromers into a three-dimensional crosslinked hydrogel that defines a hollow cylinder, wherein the cylinder is formed during polymerization of the polysaccharide macromers.

Another embodiment of the invention is a method of encapsulating an inert medical device by polymerizing a plurality of polysaccharide macromers into a three-dimensional crosslinked hydrogel that encapsulates the medical device.

Another embodiment of the invention is a method of making a medical apparatus by polymerizing heparin macromers into a three-dimensional crosslinked hydrogel and thereby making a hollow cylinder having an exterior, wherein the cylinder is formed during polymerization of the heparin macromers and the exterior is not covalently bonded to another material.

Another embodiment of the invention is a method of making polyvinylpyrrolidone polymers from polyvinylpyrrolidone macromers. Another embodiment is coating a medical device with polyvinylpyrrolidone macromers by polymerizing the macromers into a three-dimensional crosslinked polyvinylpyrrolidone material, and applying a coating that includes the crosslinked polyvinylpyrrolidone material onto the medical device.

Another embodiment of the invention is a method of making a polysaccharide polymer by obtaining or making polymerizable polysaccharide macromers, synthetically polymerizing the macromers with each other to form a group of polymers having an average length of at least two macromers per polymer, and isolating the polymers.

Another embodiment of the invention is a method of making a coating on a medical device by providing a group of polysaccharide polymers having an average length of at least two macromers per polymer, putting the polymers in a solvent to make a mixture, and contacting the medical device with the mixture.

Embodiments of the invention include a material made of a hydrogel that preferably has at least 5% polymerized polysaccharide macromers by dry weight. The hydrogel is preferably covalently cross-linked such that the hydrogel remains intact in water and preferably contains at least 30% water by total weight when hydrated. The polysaccharide macromers are polymerizable while in a solution or in a suspension. Normal polymerization techniques, including free-radical, addition, and condensation polymerization, may be used to polymerize the polysaccharide macromers.

One product incorporating the present invention is a tubular member with its inner wall and outer wall covered with a hydrogel of the invention as described herein, i.e., the tubular member is "encapsulated" by the hydrogel. A preferred macromer formulation is made from heparin, the term heparin including all molecular weights of heparin, heparan sulfate, heparan sulfate proteoglycans, fragments thereof, and/or derivatives thereof. The preferred embodiment of the heparin hydrogel is at least 80% heparin by dry weight. The tubular member preferably has a diameter of less than approximately 6.0 mm when the hydrogel is hydrated and blood is flowing though the tubular member. The tubular member may be a simple plastic extrusion or a stent, but the preferred embodiment is a knitted or woven fabric substrate. The fabric substrate is preferably pre-coated to enhance the integrity and adhesion of the encapsulant and/or improve the non-thrombogenic or anti-thrombogenic properties or both of the encapsulant.

In an embodiment of the tubular member, the tubular member is pre-coated with a very thin layer of the hydrogel containing non-thrombogenic or anti-thrombogenic properties or both, the layer being applied to cover the components of the tubular member. In the case of the knitted or woven tube, these are the individual strands from which the fabric is made. The tubular member preferably has a low porosity such that blood leakage is not a paramount concern.

In another embodiment, a porous tubular member, such as one made from a fabric, is used as the tubular member. The fabric tubular member is pre-coated with a polymeric material in order to prevent blood leakage. The coated fabric tubular member is then further coated with the hydrogel containing non-thrombogenic or anti-thrombogenic properties or both. This structure imparts an extremely thin, flexible, and compliant wall that can serve as a vascular prosthesis, especially in the context of a small diameter vascular graft.

Another embodiment is a tissue engineering matrix made from a polysaccharide hydrogel. A tissue engineering matrix is, for example, a three-dimensional material that serves as a scaffold for cellular invasion or a nerve growth matrix. Examples of tissue engineering matrices include matrices for making cartilaginous body parts such as ears or joint cartilage; ligaments; scaffolds for breast tissue invasion; liver matrices; and tissue engineered blood vessels.

The present inventors have also recognized that there is a need to use better organic solvents to dissolve polysaccharides, including heparin. The use of better organic solvents allows scientists to use chemistries and chemical techniques that are more powerful than those that are conventionally used. These techniques improve the cost, quality, and efficiency of conventional techniques for making materials from polysaccharides and enable better materials to be made.

Embodiments of the invention include the use of low dielectric organic solvents and/or low boiling-point solvents for polysaccharide chemistries to make derivatives of polysaccharides, including attaching monomers to polysaccharides to make polysaccharide macromers and the use of these improved solvents for making polysaccharide hydrogels from polysaccharide macromers or polysaccharide polymers. Further, the invention may include steps for using salts to decomplex the quaternary ammonium-heparin complex.

An embodiment of the invention is a method of making a polysaccharide macromer, for example from heparin. The polysaccharide is reacted with a quaternary ammonium salt to form a polysaccharide-quaternary ammonium salt complex and then dissolved in an organic solvent with a dielectric constant less than the dielectric constant of DMSO and/or in an organic solvent with a boiling point less than DMSO. The polysaccharide-quaternary ammonium salt complex may be reacted with a chemical such as a monomer to form useful derivatives. The polysaccharide-quaternary ammonium salt complex may then be treated with another salt to remove the quaternary ammonium salt.

The invention optionally includes steps of using a vacuum to remove the organic solvent of the invention from the polysaccharide, derivatized polysaccharide, or complexes of the polysaccharide. The vacuum removal is preferably performed at room temperature without adding heat. Alternatively, heat may be applied to evaporate the solvent, preferably enough heat to raise the temperature of the solvent to its boiling point without denaturing the heparin such that its biological activity is substantially reduced, a temperature that may vary according to the solvent used but typically being a temperature of less than approximately 100 degrees Centigrade and preferably less than 70 degree Centigrade. Alternatively, a mix of vacuum and heat may be used.

A preferred embodiment of the invention uses an organic solvent that has a boiling point at atmospheric pressure and a dielectric constant that are less than conventionally used organic solvents. A more preferred embodiment has a boiling point of less than approximately 115 degrees Centigrade and a dielectric constant that is less than that of DMSO. A more preferred embodiment uses an organic solvent that has a boiling point of less than approximately 70° C. at atmospheric pressure and a dielectric constant that is less than that of DMSO.

The invention includes polymerizing the polysaccharide macromer in an organic solvent of the invention to make a polymer of at least two macromers. The macromers may be the same or different, to thereby make a homopolymer or a copolymer. The invention includes making a hydrogel from the polysaccharide macromer and/or polysaccharide macromer, preferably in an organic solvent of the invention.

BRIEF DESCRIPTION OF THE DRAWINGS

FIG. 9 depicts a reaction scheme for making and using polysaccharide macromers.

FIG. 10 depicts an alternative reaction scheme for making and using polysaccharide macromers.

DETAILED DESCRIPTION OF THE PREFERRED EMBODIMENTS

Figure 1:
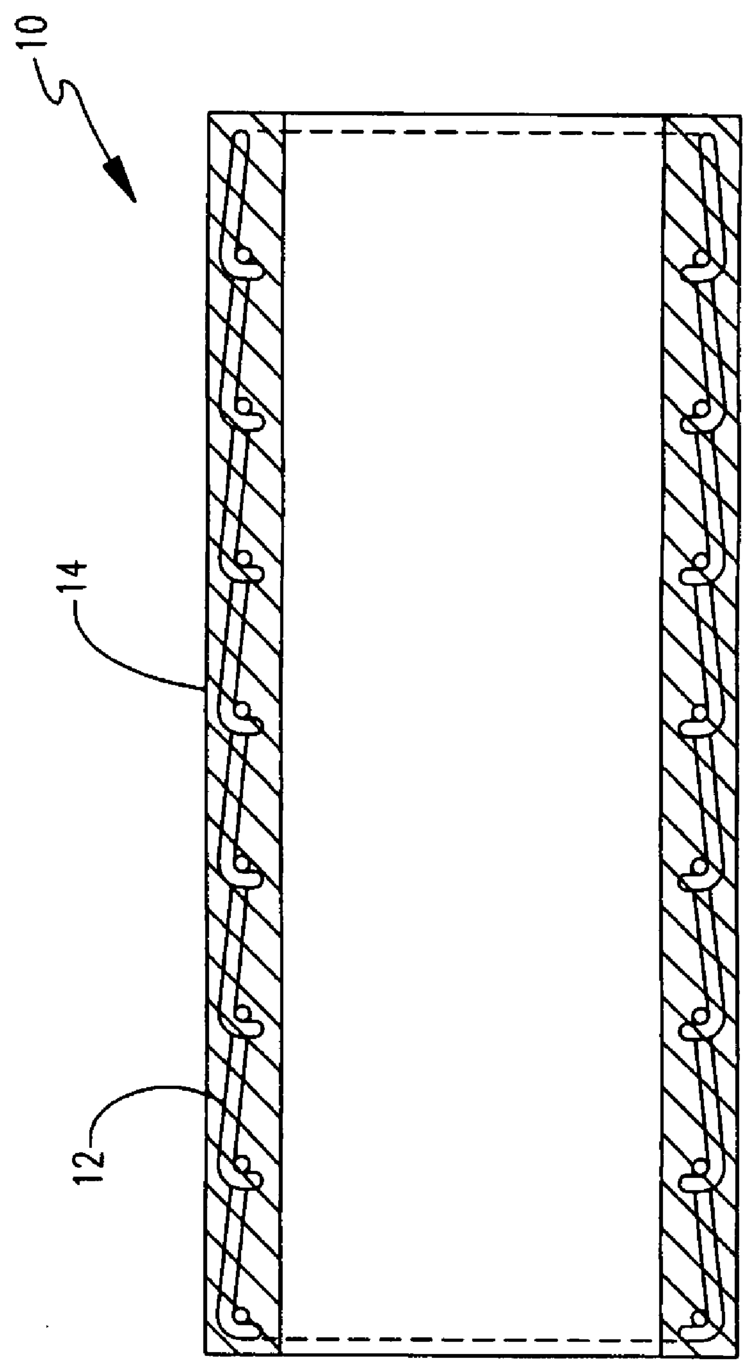
FIG. 1. is a longitudinal sectional view of an embodiment of the invention having a fabric graft encapsulated within a hydrogel.

Synthetic materials implanted into the soft tissue of a patient elicit a range of undesirable reactions that are typically categorized as acute inflammation, chronic inflammation, the formation of granulation tissue, foreign body reaction, and fibrosis (Ratner et al., 165-173, Biomaterials Science, 1996 Academic Press). Other reactions are possible, such as an immune system response or systemic toxicity and hypersensitivity. At a materials-blood interface, the blood coagulation mechanism can be activated to cause local clotting and downstream events such as complement activation or generation of blood clots (Ratner et al., 193-199). These reactions impact how synthetic articles, including vascular grafts, are designed and manufactured.

Current medical practices for the use of synthetic articles as vascular grafts are essentially restricted to the use of polyester and polytetrafluoroethylene tubes as replacements for large-diameter blood vessels to treat patients with certain types of vascular disease.

Vascular disease takes many forms, but one of the most common is stenosis, where an artery becomes narrowed by build up of plaque. Atheroscherotic Stenosis is a condition where the artery becomes hardened and less flexible by the process of calcification. The condition is often accompanied by a build up of tissue or plaque on the inside wall of the lumen of the artery. This build up causes the lumen of the artery to narrow and restrict the passage of blood.

Total occlusion of an artery may occur when a clot of blood (a thrombus) lodges inside an artery, at a narrowing. Such occlusions can prove fatal if the artery is in a critical position; for example, coronary thrombosis causing a heart attack, or cerebral thrombosis causing a stroke.

Even if there is not total occlusion, a restriction of the flow of blood can cause severe problems in limbs and organs downstream from the stenosis, due to starvation of the oxygen and nutrients supplied by the blood. A very common example is the reduction of flow in the lower leg, which may lead to claudication and eventually to gangrene and loss of a limb.

A higher profile example of stenosis is observed when the disease affects the coronary arteries, which supply blood to the muscle of the heart. Stenosis, or occlusion due to thrombosis, can lead to an infarction due to parts of the muscle tissue of the heart dying (necrosis). That is, a myocardial infarction or heart attack.

Another common form of vascular pathology is an aneurysm. An aneurysm is a condition where the wall of the artery weakens and dilates to form a balloon-like swelling. An aneurysm is a weakening of the artery wall leading to dilation. This dilation can develop so that the arterial wall is too thin and weak to withstand the pressure of the blood. A burst aneurysm causes severe hemorrhage, and can be fatal. One example is the so-called AAA (triple A) or abdominal aortic aneurysm; rupture of an artery having this defect is almost always fatal.

Conventional vascular surgery techniques have made the surgical replacement of diseased arteries commonplace. The use of autologous grafts where a non-essential vein from a person's own blood vessels is used as a replacement artery is the oldest form of vascular grafting, and is still used today especially for coronary bypass procedures. A patient, however, may not have enough autologous donor vessels to fill the needs of the replacement surgery. Further, it is desirable that there be an alternative to the loss of a functioning blood vessel. It was the development in the 1960s of synthetic fabric prostheses, which led to the range of products available to the vascular surgeon today.

Conventional synthetic vascular grafts are woven or fabric seamless fabric tubes, which are used as a direct replacement for a section of diseased artery. Various materials have been tried, but the most successful is polyester, which is the only material now used by clinicians for fabric grafts. Polyester is a very bio-stable material and, although slightly thrombogenic, is reasonably well tolerated in use for larger diameter arteries (approximately 6-mm diameter and above).

When implanted, a vascular graft causes the body to react and generate a blood clot layer around its inner perimeter. This blood clot may be accompanied by tissue growth. If such tissue growth is not securely anchored in place, there is a danger of a loose blood/tissue clot or embolus being formed. The flow of blood may carry the embolus downstream until it reaches a narrower part of the artery where it may cause a blockage or occlusion.

In order to ensure that tissue growth remains anchored to the graft, fabric grafts are made slightly porous so that the tissue grows into the pores of the fabric and is firmly attached. This has an added advantage that the tissue encapsulates the fabric graft and covers it, using the graft as scaffolding for new growth. In general, grafts with higher porosities, and especially flexible and elastic fabric grafts, heal better and generally perform better than low porosity woven grafts. It is because of this effect that the so-called "velour" grafts have been developed. Velour grafts have textile filaments raised up on the surface of the fabric.

The need for porosity creates an initial problem for the surgeon since a high porosity graft will leak if simply implanted with no special preparation. After implantation, tissue growth fills in the pores in the fabric and therefore renders the graft "blood tight". The problem is to make the graft blood tight during the initial surgery and for the immediate few hours afterwards. The original approach taken was to "pre clot" the graft before implantation. A small amount of blood was taken from the patient before the operation, and the graft was soaked in this blood so as to fill all the pores of the fabric with clots. The porous structure ensured that the clotted blood was firmly attached. This procedure was, however, time consuming, and it was and is very difficult to properly pre-clot those materials with high porosities. Because of these problems, the soft and very compliant fabric grafts, which heal better than stiff woven grafts, were not considered suitable for areas of high pressure such as thoracic arteries near the heart.

Subsequent to the development of fabric grafts, a new development was introduced. The invention of the graft made from polytetrafluoroethylene (PTFE). PTFE is a material that is generally well tolerated in the body. A chief advantage with a PTFE graft is that it does not require pre clotting. However, PTFE material does not heal as well as warp fabric grafts. Modern PTFE prostheses are made of expanded material in order to imitate the cellular structure of fabric grafts, but this is only partially satisfactory.

Fabric grafts are now available which do not require preclotting. They are coated with a bio-absorbable material such as gelatin or collagen. The coating material is gradually adsorbed and tissue grows to replace it. Such grafts are not only simpler to use because there is no requirement for preclotting, but they also tend to give better healing and performance.

All of these conventionally used grafts have a common disadvantage in that they cannot be used for small diameter applications. Synthetic vascular grafts with a diameter of less than approximately 6 mm will not remain functional over a clinically significant period of time.

The reason for the failure of conventional small diameter vascular grafts is thought to be related to the flow rate and type of blood flow within the graft. With a large inner diameter graft, there is a high volume of blood passing though the vessel. Any small tissue growth on the inside wall is insignificant and does not disrupt flow. With small inner diameter grafts, a small tissue build up is more significant in relation to the overall diameter of the vessel. A small build up will cause flow turbulence, which, because of the already low volume flow, tends to cause even more tissue growth, which leads to stenosis.

Conventional medical clinicians urgently need a small diameter synthetic graft to cope with a range of small caliber replacement requirements. The only procedure conventionally available is an autologous transplant of the saphenous vein in the leg. The problem with this approach is that the amount of graft material available is very limited. In addition, the removal of the saphenous vein causes severe discomfort to the patient. One of the most important of these small diameter applications is the replacement or bypass of coronary arteries in cases of coronary stenosis. Another use is for the replacement of stenosed or occluded infragenticulate arteries.

In order to replace the smaller caliber vessels using a small diameter vascular graft, the implant should be highly biocompatible and not thrombogenic. The biocompatibility should be such that little tissue growth is stimulated and the blood and body accept the prosthesis in a similar way that they accept the natural artery.

Many polymers have been tested for the small diameter vascular graft application. A polymer is a single molecule built up by the repeated reaction of molecules that may be referred to as monomers. Monomers are molecules that may be reacted with other monomers to make a polymer. For example, a methylmethacrylate monomer represented by "A" may be used to make polymethylmethacrylate, which would be the polymer "AAAAA". A polymer made of monomers A and B could have a random structure of ABAAABAABA and could be called a polymer or a copolymer of A and B. Polymer AAAAA and BBBBB could be joined to form copolymer AAAAABBBBB. A molecule that is derivatized is a molecules that has been chemically changed; a molecules that has been decorated is a molecules that has had a chemical unit attached.

A macromer, as used herein, is a monomer or a polymer that is polymerizable and is a convenient term for referring to monomers or polymers that have been decorated with a monomer or used as decorations. Polysaccharide macromers include multiple polysaccharides that are polymerizable. For example, several macromers may be polymerized together to form a larger polymerizable group that is a macromer. Or several polymers, e.g., polysaccharides, may be joined together and decorated with polymerizable groups to form a macromer. Thus a heparin macromer is a heparin molecule that is polymerizable, for example after being decorated with a monomer. The term polymer, as used herein, includes oligomers and chains of at least two monomers in length. Polymers can be assembled into larger materials; for example, many polymers may be linked together to form a hydrogel.

A variety of hydrogels are blood compatible. Examples that are commercially useful are made from polyhydroxyethylmethylacrylate (PHEMA), polyacrylamides, polyacrylic acid, N-vinyl-2-pyrrolidone (NVP), methacrylic acid, methyl methacrylate, and maleic anhydrides, each of which have been proven to be polymerizable from monomers. Further examples of biocompatible materials include hydrogels made from polyvinyl alcohol, methacrylates in general, acrylates in general, polyethylene glycol (PEG), hyaluronic acid, and alginates.

The term hydrogel, as used herein, is a cross-linked material that can absorb or imbibe a water and is produced by the cross linking of one or more monomers or polymers. The cross-links in a hydrogel may be the result of covalent bonding or of association bonds, for example hydrogen bonds, charge-charge interactions, or strong van der Waals interactions between chains (Ratner et al., pages 60-64). A hydrogel cannot be suspended in water nor does it dissolve in water; instead, it remains intact water. For example, a material can shrink or swell and still remain intact without dissolving. For example, a contact lens shrinks and swells in water but does not dissolve therein.

Hydrogels have been used for a myriad of applications, such as artificial tendon materials, wound-healing bioadhesives, wound dressings, artificial kidney membranes, articular cartilage, knee cartilage replacement, artificial skin, maxillofacial and sexual organ reconstruction, tissue engineering scaffolds, and vocal cord replacement materials. There are many types of hydrogels known to those skilled in these arts, such as aerogels, xerogels, equilibrium-swollen hydrogels, solvent-activated hydrogels, and swelling-controlled relapse hydrogels (e.g., Ratner et al., page 60-64). These types of hydrogels may be used with certain embodiments of the invention. Moreover, all of the uses for hydrogels described in this application may be used in certain embodiments of the invention.

Polysaccharides are polymers made from monomers that are sugars. Alginate is a polysaccharide. Glycosaminoglycans are a subcategory of polysaccharides that are made from repeats of disaccharide units. Glycosaminoglycans include hyaluronic acid, chondroitin sulfate, dermatan sulfate, heparan sulfate, heparin, chitin, chitosan, and keratan sulfate. Polysaccharides and glycosaminoglycans can also be found in a related proteoglycan form; proteoglycans are polysaccharides unified with a protein. Methods, compositions, and uses as described herein for polysaccharides are applicable to proteoglycans, glycosaminoglycans, and natural or synthetic derivatives or fragments thereof.

Heparin is a polysaccharide polymer with an important property: it interferes with key molecules in the blood clotting mechanism such that the blood will not clot. Coating the inside of a tube with heparin tends to increase the amount of time that the tube remains open to blood flow but, to date, small diameter vascular grafts coated with heparin have failed to resist blockage by blood coats for a clinically useful length of time. Many researchers have tried to use heparin to coat the inside of vascular grafts. Heparin is a molecule that belongs to a group of molecules called polysaccharides that are molecules made from combinations of smaller molecules called sugars. Polysaccharides are naturally-occurring polymers but the present invention also contemplates synthetic, derivitized, man-made, and semi-synthetic polysaccharides.

Heparin has been applied to materials in many ways. General strategies have included adsorption, making charge-charge bonds with the surface, covalent immobilization, and release from a surface. Photoactivatable chemical groups have been put onto heparin so that if heparin is put close to the surface and the surface is bathed in light to make the photoactive groups make permanent covalent chemical bonds with the surface. Similarly, heparin has been reacted with polymerizable monomers that have then been reacted to achieve covalent bonding to the surface.

Despite the great amount of research effort that has been expended in the field of biomaterials, including research with hydrogels, heparin, and polysaccharides, there is a continued need for improved biomaterials. Biomaterials that may be used in blood-contacting applications are especially required.

The invention provides embodiments that include an improved biomaterial that successfully combines the advantages of polysaccharides and hydrogels. One embodiment of the invention is a hydrogel made of polysaccharides. Another embodiment is a linear or multi-armed polysaccharide or polyvinylpyrrolidone polymer that is absorbable to a surface. Multi-armed means a soluble polymer that is branched or cross-linked. The hydrogels and the coatings may be used for the many applications for which a hydrogel may be used, e.g., as already described. There are other uses for hydrogels and the linear or multi-armed polymers that include coatings for stents, catheter coatings, cardiac valves or leaflets, cartilage replacement, replacement knee cartilage, organ scaffolds, lumbar disks, cell encapsulation, wound healing, nerve guides or tubes, and postoperative adhesions. A hydrogel may be used to make, coat, or encapsulate such devices. A coating may be used to such devices to improve their performance. Another hydrogel use is for a wound dressing for large, shallow wounds on animals so that a scab does not form over the wound but prevents blood clotting at the surface, thereby preventing scar formation.

The hydrogel may be made by mixing polysaccharide macromers, e.g., heparin macromer, with other macromers or monomers to make a mixture. The mixture is poured into a mold and polymerized. After polymerization, the mold is removed and the polymerized macromers/monomers are hydrated. Various shapes, e.g., sheets, tubes, spheres, rods, may be formed by using suitable molds.

The resultant shape is not covalently or otherwise bonded to other materials: the exterior and luminal surfaces are "free". The free surfaces are not attached to other surfaces. A free surface may be decorated with moieties, e.g., drugs, polymers, and other agents. Such decorations do not cause the free surface to thereby be attached to other materials. Further, the resultant shape is formed during the polymerization process. This shape-forming process is distinct from processes that build up a coating on the inside of, e.g., a tube, in part, because the coating on the tube is essentially inseparable from the tube, especially if it is ionically or covalently bonded thereto.

Moreover, the prior art methods of applying a coating to a tube and building up the coating is not equivalent to the present process. First, the prior art coating procedure does not create the tubular shape. But polymerizing macromers of the invention into a tubular shape during the polymerization process does create the tubular shape. Making a shape during a polymerization process is difficult because the polymerization reaction must be effective enough to make a solid material, with the effectiveness depending on polymerization variables known to those skilled in these arts. For example, an effective process requires using a macromer that can be provided in sufficient concentration. Not all macromers are sufficiently soluble to be present in solution with a high enough concentration to make a solid. The polymerization mixture must have be crosslinkable for crosslinks to form. The kinetics of the polymerizable groups must be suitable.

Many prior art processes have not overcome these limitations and instead dry polymerizable groups onto a surface and then crosslinking them. The drying step results in drastically different structures than those made with polymerization from a solution (or a melt). If proteins or polysaccharides are dried, they aggregate and form clumps on the molecular level. In contrast, polymerization from a solution gives structures that are not aggregated but instead have a network of unaggregated polysaccharides. Since the macromers are not aggregated, the density of materials polymerized from solution can be lower. Moreover, a true polymerization process may take place wherein the polymerizable groups react with each other to form a polymeric backbone. In contrast, dried solutions have little mobility and the polymerizable groups react with the chemical structures closest to them instead of reacting with other polymerizable groups.

In short, chemical crosslinking is not equivalent to polymerization. The present materials and methods provide for polymerization methods and for polymerized materials as opposed to coatings built up on surfaces, gelled structures, and merely aggregated, chemically crosslinked, or surface-immobilized materials. The advantages of polymerization are numerous and well known to ordinary artisans.

One advantage of a polysaccharide covalently polymerized with a hydrogel is that the polysaccharide may be stably incorporated into the hydrogel so that it is not released over time. This stability is useful for a long-term implant because the hydrogel would otherwise dissipate over time and eventually fail. The heparin hydrogels of the present invention are hypothesized to function by reversibly binding antithrombin III. The antithrombin III is bound by the heparin and thereby changes its shape so that it reacts with and inactivates both thrombin and Factor X(a), which are key enzymes required for blood to clot. The antithrombin III is hypothesized to stay on the heparin hydrogel temporarily so that it attaches, reacts with thrombin and Factor X(a), and departs back into the bloodstream so that a new antithrombin III molecule may be bound to the heparin.

Another advantage of the polysaccharide hydrogel is that it can be made as a thick film. Thick films may be handled by surgeons, grasped with tools such as forceps, punctured by sutures, and suffer scratches and damages to their surface without losing their favorable blood-contacting properties. The thickness of the film and the three-dimensional structure of the film allows it to suffer minor damage while continuing to cover the surface with heparin molecules. In contrast, damage to a thin coating or a synthetic material that has been merely reacted with a polysaccharide can entirely remove the polysaccharide and expose the underlying material to the body. For example, a surgeon that uses forceps to firmly grasp a plastic tube covered with a layer of heparin that has been reacted with the tube's surface might accidentally scratch the tube and remove the heparin thereby exposing the underlying plastic material of the tube. In contrast, a surgeon might accidentally scratch a plastic tube encapsulated with a thick film heparin coating of the present invention but would not thereby expose the underlying plastic because a scratch in the thick film would expose only more of the heparin hydrogel.

Further, the thickness of the hydrogel film is hypothesized to minimize blood contact with the synthetic material that the thick film is encapsulating. Blood or its components must penetrate through the entire thickness of the hydrogel prior to reacting with the encapsulated synthetic material. In contrast, a thin coating, especially a coating of a few molecules' thickness, presents a shorter distance between the blood and the encapsulated synthetic material. This distance is important because the efficiency of surface chemistry reactions used for conventional techniques is hypothesized to typically provide a surface coverage of less than 100%, i.e., not every space on a surface coated with heparin is completely covered with a heparin molecule. In contrast, a thick film of the present invention provides more than 100% coverage because any molecule that would react with the surface must pass through a thick coating that has a thickness of many molecules.

One embodiment of the invention is a tubular member encapsulated by a polysaccharide hydrogel. The encapsulation may be achieved by a number of processes, one such process being placing tubular member into a mold and charging the mold with the desired formulation of polysaccharide macromers and polymerized by conventional techniques at room or at elevated temperature and/or by electromagnetic radiation. A material that encapsulates a member is termed an encapsulant.

Certain embodiments of the invention involve polymerization processes, including polymerization of polysaccharide macromers. The polysaccharide macromers may be polymerized using conventional techniques, for example using initiators, carriers, accelerators, retardants, viscosifiers, and/or cross-linkers. The polysaccharide macromers may also be copolymerized with and other monomers and/or macromers and/or polymerizable polymers. In another embodiment, a tubular member is covered with a mixture of polysaccharide macromers and/or monomers and/or polymers. The polymerizable groups are subsequently polymerized to form a crosslinked hydrogel. It may be desired to placed the tubular member on a rotating mandrel and apply the mixture so as to ensure that the tubular member is encapsulated uniformly.

The polysaccharide macromers and polymers made thereof may also be copolymerized, blended, mixed, and/or cross-linked with other monomers and/or macromers, and/or polymers including engineering polymers, blood compatible polymers, hydrogel polymers, natural polymers (e.g., deoxyribonucleic acid, polysaccharides, and proteins and bioactive fragments thereof) and/or fillers. The type of initiation is not limited and may include thermal, X-ray, ultraviolet, infrared, visible light, free radical, addition, sonic, and condensation initiation.

Monomers for mixing with the polysaccharide macromers can include, but are not limited to, monomers with hydroxyl groups (e.g., hydroxyethyl methacrylate), monomers with glycerol groups (e.g., glycerol monomethacrylate, glycerol dimethacrylate, glycerol trimethacrylate), monomers with polyoxyalkylene ether groups (e.g., polyethylene glycol methacrylate, polypropylene glycol methacrylate), monomers with vinyl groups (e.g., N-vinyl pyrrolidone), monomers with zwitterionic groups (e.g., 2-methacryloyloxyethyl-2-(trimethyl ammonium) phosphate, monomers with silicone groups (e.g., methacryloxypropyl tris (trismethyl-siloxy) silane and other silicone methacrylate or acrylates), monomers having sulphate groups (e.g., vinyl sulphonic acid), monomers having sulphonate groups (e.g., ammonium sulphatoethyl methacrylate), heparin monomer as cited in the patent PCT GB9701173 and U.S. Pat. No. 6,096,798, which are hereby incorporated herein by reference.

Polymers for mixing, blending, and/or copolymerization with polysaccharide macromers include derivatized polymers, for example, derivatized polyoxyalkylene ether groups (e.g., polyethylene oxide terminating in hydroxyl group, carboxylic groups and/or isocyanate groups and polypropylene oxide terminating in hydroxyl group, amino groups, carboxylic groups and/or isocyanate groups), polyvinyl pyrrolidone functionalized with methacrylate groups, methacrylate terminating dimethysiloxone, vinyl terminating dimethylsiloxone, polyurethane terminating in isocyanate, polyester terminating in isocyanate and also other polymers that can be derivatized with methacrylate, acrylate, isocyanate, carboxylic acid, amino, hydroxyl and/or vinyl groups.

Polymers mixed, blended and/or copolymerized with polysaccharide macromers may also be used to enhance the viscosity of the mixture formulation for the application to the rotary mandrel and hence the polymerization of the mixture formulation. This technique may be used to give the encapsulated tubular member a homogenous and smooth surface, a feature that enhances vascular prosthesis biocompatibility. The encapsulated tubular member and hence the biocompatible vascular prosthesis has a smooth surface containing non-thrombogenic or anti-thrombogenic properties or both and preferably has a water content ranging from about 30% to about 90%.

Figure 2:
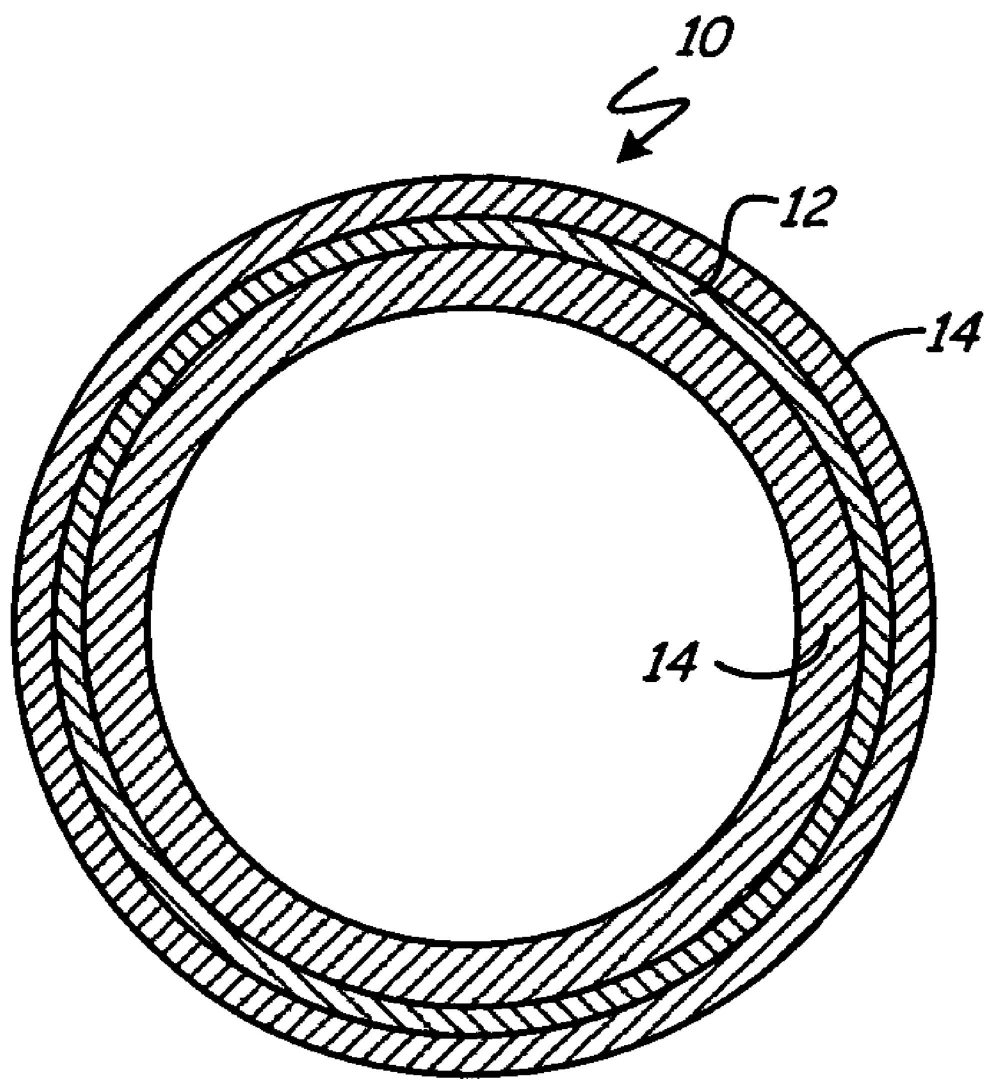
FIG. 2. is a side elevational view of the structure depicted in FIG. 1.

In a first preferred embodiment of the invention, a tubular member is encapsulated by the hydrogel, e.g., as in FIGS. 1 and 2, the hydrogel having cross-linked polymers made from polysaccharide macromers and copolymerized with monomers from at least three of these classes, as discussed in patent application PCT GB97 01173, U.S. Pat. No. 6,096,798: (a) monomers having sulphate groups, (b) monomers having sulphonate groups, (c) monomers having sulphamate groups, (d) monomers having polyoxyalkylene ether groups and (e) monomers having zwitterionic groups. The polysaccharide macromers are preferably heparin macromers. Hydrogel encapsulation of the tubular member is performed by placing the tubular member into a mold, adding a macromer and/or monomer formulation and then polymerizing to make a hydrogel. The monomer constituents may vary from 10% to 90% by weight and are preferably polymerized with a bifunctional monomer, e.g., ethylene glycol dimethacrylate. This formulation provides the prosthesis with a smooth surface, prevents the leakage of blood, is non-thrombogenic and/or anti-thrombogenic, and has a water content ranging from 30% to 90% when hydrated. When hydrated, the biocompatible vascular prosthesis is soft and pliable so it will not compromise the mechanical properties of the prosthesis.

FIG. 1 depicts a longitudinal cross section of a small diameter vascular graft 10 according to a first preferred embodiment of this invention. FIG. 2 shows an end view of a radial cross section of FIG. 1. The loops of synthetic material 12 are completely encapsulated within hydrogel 14. This embodiment is suitable for porous members that allow passage of the macromer and/or monomer constituents through the pores of the tubular member, e.g., a fabric, in order to provide binding between the inner and outer faces of the encapsulant.

Figure 3:
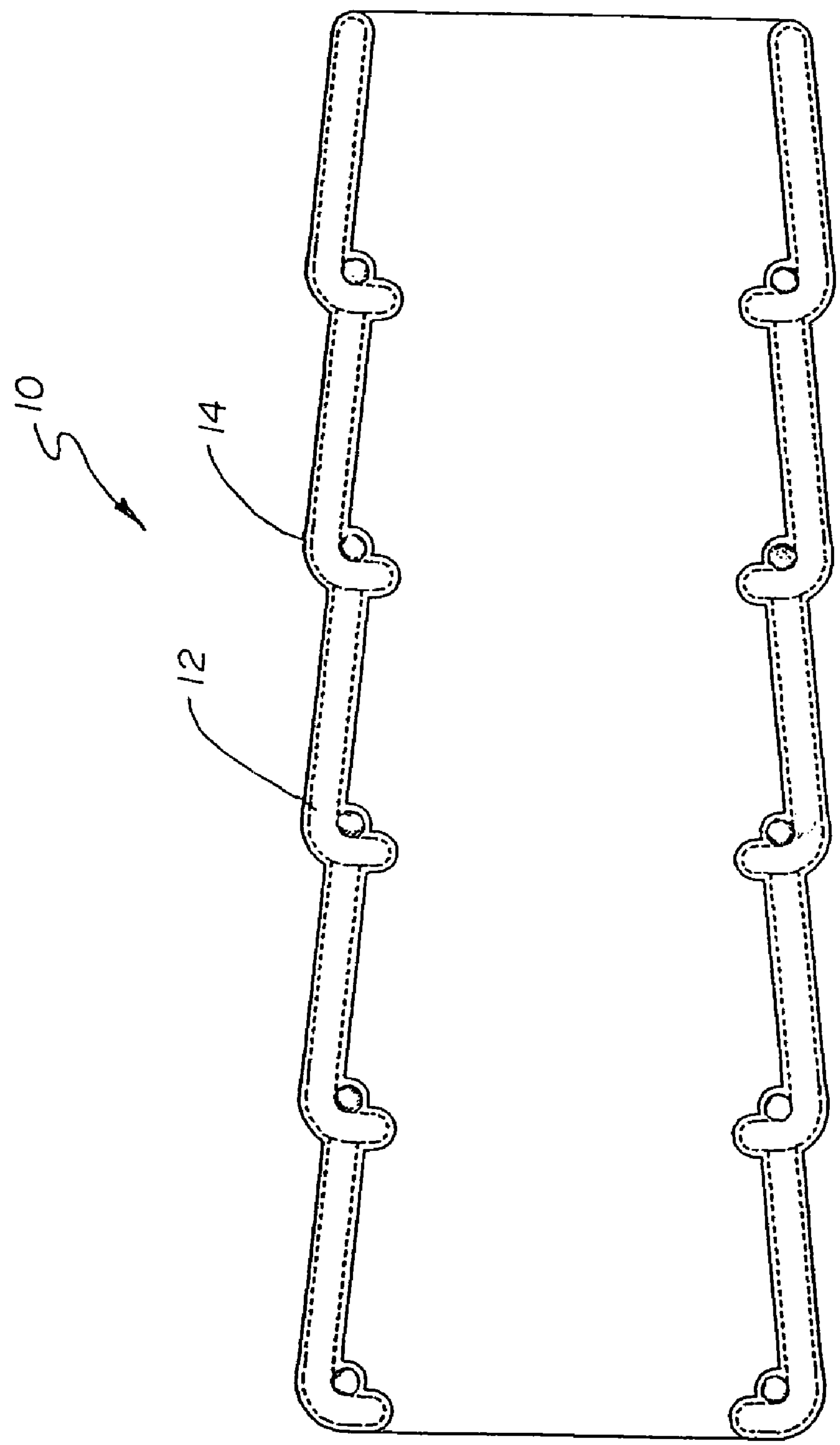
FIG. 3. depicts a longitudinal sectional view of an alternative embodiment of the invention having a fabric graft coated with a hydrogel of the invention.

An alternative to the first preferred embodiment of the invention uses approximately the same materials and methods but a tubular blood vessel member 13 is used which has sufficiently low porosity so that blood leakage is not a consideration. e.g., a tightly knitted or woven fabric, or a plastic extrusion. With this kind of tubular member, the basic porosity is low. Referring to FIG. 3, instead of encapsulating tubular member 13, it is covered with a hydrogel layer 14 of polysaccharide macromer and/or monomers. In the case of a fabric tubular member, the hydrogel coats the individual yams and fibers. At the same time, the hydrogel may be used to cover the pores completely or partially. The loops of knitted fabric 13 are coated by hydrogel 14. This embodiment is simpler to make than the encapsulation process as the covering is applied by dip process, spraying technique or by other conventional process.

Figure 4:
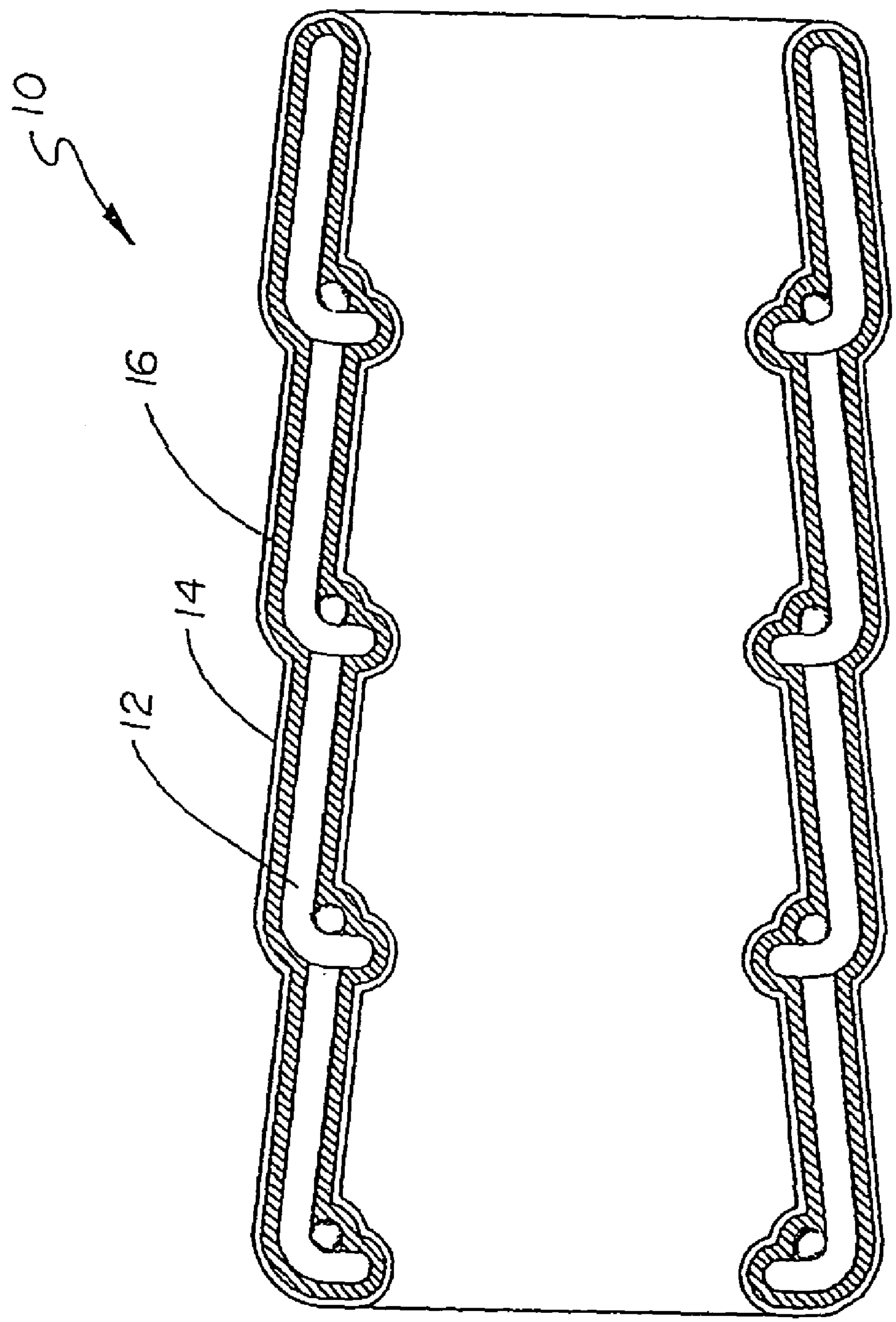
FIG. 4. depicts a longitudinal sectional view of another alternative embodiment of the invention having a double-coated fabric graft.

A second alternative to the first preferred embodiment of the invention uses approximately the same materials and methods but uses a porous tubular member 15, such as one made from a fabric, which is pre-coated (a primary coating layer 16) with a polymeric material in order to prevent blood leakage, as the layer provides a strong "leak proof" security layer (FIG. 4). The leak proof layer is essentially impermeable to blood, meaning that it generally prevents flow of blood in surgical applications. Alternatively, the barrier may be permeable to blood, and control the flow of blood. Primary coating layer 16 may be made from a number of flexible polymers, e.g., silicone polymer, polypropylene, polyester, polyurethane, polytetrafluoroethylene (PTFE) or elastomeric polymer such as silicone rubber. The total composite is then further coated with hydrogel 14 containing polysaccharides. This structure imparts an extremely thin, flexible, and compliant wall to vascular prosthesis 10. Each of the coating processes may be applied by dip process, spraying technique or by other conventional coating process. FIG. 4 depicts a longitudinal cross section of a knitted tubular member coated according to this embodiment. The fabric loop of porous tubular member 15 is inside primary coating 16, which in turn is inside hydrogel 14.

Figure 5:
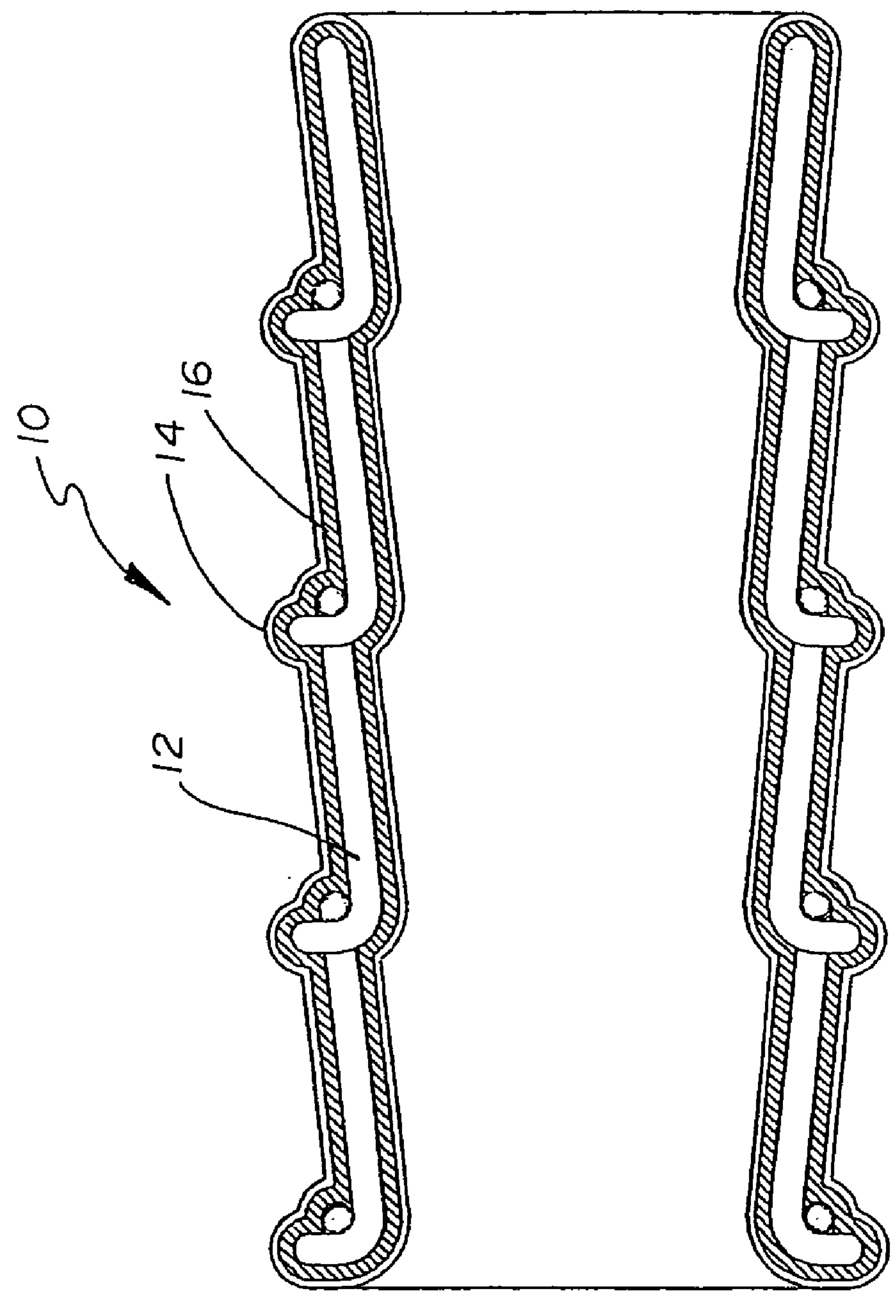
FIG. 5 depicts a longitudinal sectional view of another alternative embodiment of the invention like the embodiment of FIG. 4 except that the fabric graft tube has been inverted.

Referring to FIG. 5, another embodiment of the invention takes advantage of the manufacturing processes of woven vascular prostheses. A tubular member made from knitted fabric has a different surface texture on the internal face and the external face. The technical face of the fabric tends to be smoother than the technical back. In the case of the knitted tubular member, the technical back is on the internal face of the fabric, whereas the technical face is on the external face. When used as a vascular prosthesis, the knitted tubular member can be inverted so that the smoother face is on the internal face of the prosthesis. In addition, the internal face has very shallow grooves, which run longitudinally. These grooves may help to smooth the flow of the blood and reduce turbulence.

FIG. 5 shows a schematic longitudinal cross section of a porous tubular member 15 made of a knitted material that is coated with the fabric inverted. The fabric loop of the porous tubular member 15 is inside the primary coating 16, which in turn is inside the hydrogel 14. A tubular vascular vessel made from knitted fabric has a different surface texture on the internal face and the external face. The technical face of the fabric tends to be smoother than the technical back. In the case of the knitted tubular member, the technical back of the fabric is on the internal face of the vessel, whereas the technical face is on the external face of the vessel. The fabric loop of the porous tubular member 15 is inside the primary coating 16, which in turn is inside the hydrogel 14.

A most preferred tubular member is a warp knitted or weft knitted seamless fabric tube. In the warp knitted form, the most preferred structure is reverse locknit, but tricot can also be used. The fabric tube can also be weft knitted or woven. The tube may be continuous or it may be bifurcated in order to fulfill the needs of a graft designed to replace the Aorto-Iliac bifurcation.

Figure 6:
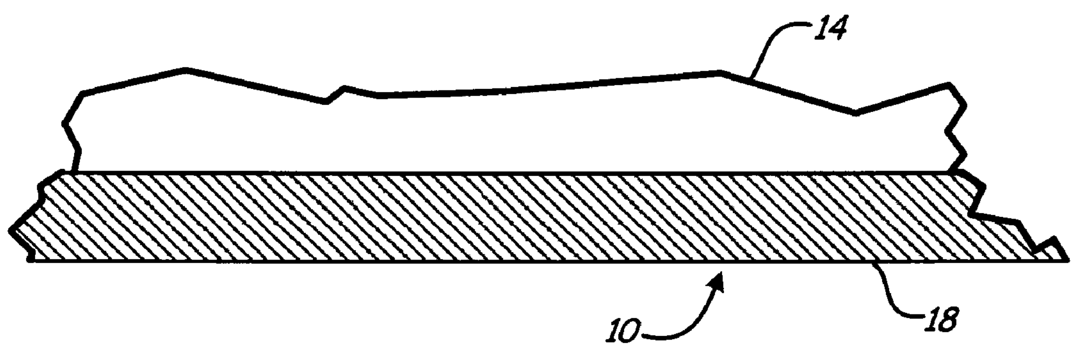
FIG. 6 depicts a partial view of an alternate embodiment of the invention having a plastic surface coated with a hydrogel.

FIG. 6 shows a portion of a vascular graft 10 with surface 18 with a thick film of hydrogel 24. The thickness of film 24 protects surface 18 from being exposed as a result of damage caused by handling the vascular graft 10. The film is preferably at least 25 μm thick, more preferably from about 5 to about 1500 μm thick, and even more preferably about 500 to about 800 μm thick.

Alternatively, a very thin coating or hydrogel may be applied to a graft or other structure. The coating is applied, e.g., by spraying, so that the coating or hydrogel is present on the fibers of the graft. The interstices between the fibers are not coated by this technique. For example, a wire mesh stent may be coated with a hydrogel without the hydrogel filling the interstices of the mesh. Such a hydrogel or coating is preferably less than about 10 μm in thickness.

Figure 7:
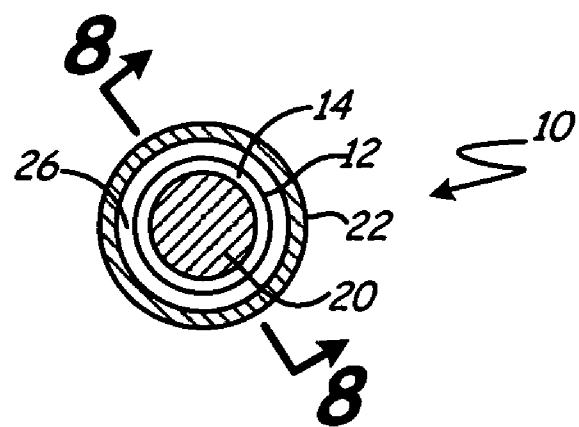
FIG. 7 depicts a cross-sectional view of a hydrogel of the invention being formed on a mandrel.
Figure 8:
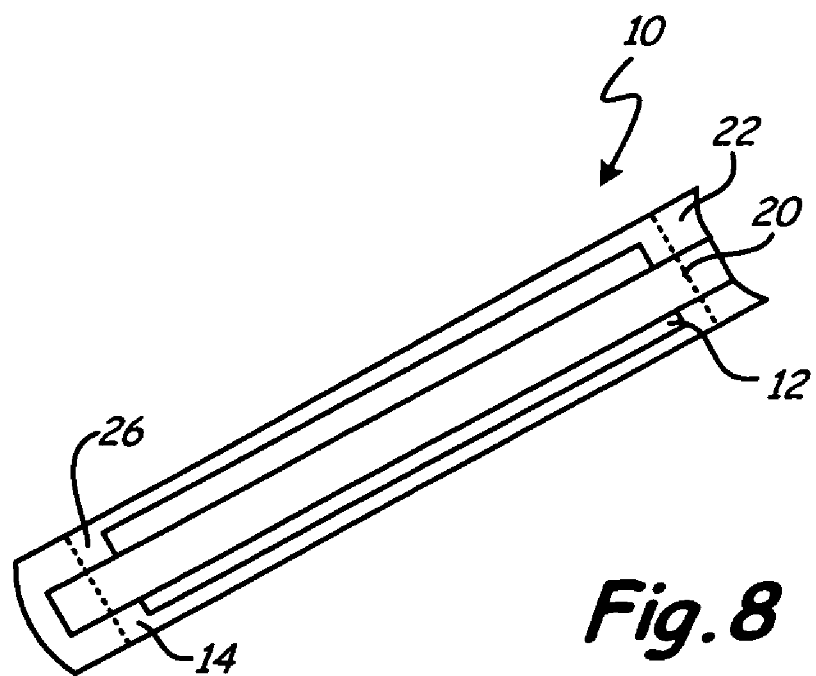
FIG. 8 is a sectional view of FIG. 7.

FIG. 7 depicts vascular graft 10 being made by molding hydrogel 14 around mandrel 20 and within outer mold 22 while entrapping synthetic material 12 in annulus 26 created by mandrel 20 and outer mold 22. The monomers and/or macromers used to make hydrogel 14 are poured into annulus 26 and then polymerized around synthetic material 12. FIG. 8 depicts cross-section 8-8 of FIG. 7; hydrogel 14 is shown in phantom lines.

A tubular member of the invention may also be a plastic tubular extrusion of a polymeric material. Such materials could be, for example, silicone polymers, polyester, polyurethane, polypropylene, silicone elastomer, polytetrafluoroethylene (PTFE) or other suitable materials. The tubular member may also be porous or have a defined permeability, e.g., as a hollow tube fiber with a defined molecular weight cut-off. Porosity/permeability may be incorporated into a tube by the selection of the material or by adding pores or holes, e.g., by lasers, and punctures.

Another embodiment of the invention is a method of making a vascular graft. A first polysaccharide hydrogel tube is made and introduced inside of a tubular member that has an exterior side and an inner side that faces the lumen of the tubular member. A second polysaccharide hydrogel tube is made and introduced around the outside of the tubular member to form a sandwich of a tubular member between two hydrogel tubes. The two hydrogel tubes are then treated to form one unit. One suitable treatment is to swell the hydrogel tubes in a solvent to bring them in to contact with each other and then to chemically react them. Examples of suitable chemical reactions include polymerization, polymeric cross-linking with ultraviolet, heat, or sonic initiators, and chemical cross-linking with gluteraldehyde, or diisocyantes. The cross-linking agents may be present in the tubes prior to swelling or may be introduced with the solvent. Suitable solvents include aqueous solvents, organic solvents, and low boiling point and/or low dielectric constant organic solvents. One option for forming one unit of the hydrogels is to use a tubular member that is shorter than the two hydrogel tubes so that the two hydrogel tubes are joined around the tubular member. Another option for forming one unit of the hydrogels is to use a tubular member that is porous so that the hydrogels are forced into the pores during swelling so that the two hydrogel tubes contact each other through the pores. As a result, the hydrogels may become cross-linked through the pores.

The polymers and hydrogels of the invention, whether encapsulating or coating the tubular member, may if desired, incorporate and slowly release growth factors, thrombolytic drugs, thrombotic drugs, enzymes, restenosis-preventing drugs, inhibitors and other agents used to treat diseased tissues. Further, gene therapy delivery may be performed by complexing gene therapy victors to the polymer or hydrogel, e.g., by complexing DNA and a polysaccharide together with a positively charged ion or polymer. Other functions, uses, applications, formulations, and technologies of hydrogels known those skilled in the art may be used to create further alternative embodiments of the invention.

An embodiment of the invention is a method of making a heparin macromer by reacting heparin with a quaternary ammonium salt to form a heparin-quaternary ammonium salt complex; dissolving the heparin-quaternary ammonium salt complex in an organic solvent with a dielectric constant less than the dielectric constant of dimethylsulfoxide; and decorating the heparin in the heparin-quaternary ammonium salt complex with a polymerizable monomer. Further, a vacuum removal step of removing the organic solvent with a vacuum may be used, preferably at room temperature.

An embodiment of the invention is a method of making a heparin macromer by reacting heparin with a quaternary ammonium salt to form a heparin-quaternary ammonium salt complex; dissolving the heparin-quaternary ammonium salt complex in an organic solvent that has a boiling point of less than 190 degree Centigrade at atmospheric pressure; and decorating the heparin in the heparin-quaternary ammonium salt complex with a polymerizable monomer. The step of dissolving the heparin-quaternary ammonium salt complex in an organic solvent is alternatively performed with an organic solvent with a boiling point of less than 114 degrees Centigrade at atmospheric pressure.

The invention includes an optional additional step of decomplexing the heparin quaternary ammonium salt from the heparin-quaternary ammonium salt complex by mixing the heparin-quaternary ammonium salt complex with a salt that is not a quaternary ammonium salt An embodiment of the invention is a method of making a heparin polymer by reacting heparin with a quaternary ammonium salt to form a heparin-quaternary ammonium salt complex; dissolving the heparin-quaternary ammonium salt complex in an organic solvent that has a boiling point of less than 190 degree Centigrade at atmospheric pressure; decorating the heparin in the heparin-quaternary ammonium salt complex with a polymerizable monomer; and polymerizing the monomer to make a polymer.

An embodiment of the invention is a method of making a heparin hydrogel by reacting heparin with a quaternary ammonium salt to form a heparin-quaternary ammonium salt complex; dissolving the heparin-quaternary ammonium salt complex in an organic solvent with a dielectric constant less than the dielectric constant of dimethylsulfoxide; decorating the heparin in the heparin-quaternary ammonium salt complex with a polymerizable monomer to make a heparin macromer; and polymerizing the heparin macromer to form a polymer and cross-linking the polymers to form a hydrogel.

An embodiment of the invention is a method of making a polysaccharide macromer, the method comprising: reacting a polysaccharide with a quaternary ammonium salt to form a polysaccharide -quaternary ammonium salt complex; dissolving the polysaccharide-quaternary ammonium salt complex in an organic solvent that has a boiling point of less than 190 degree Centigrade at atmospheric pressure; and decorating the polysaccharide in the polysaccharide quaternary ammonium salt complex with a polymerizable monomer. The step of dissolving the polysaccharide -quaternary ammonium salt complex in an organic solvent may also be performed with an organic solvent with a boiling point of less than 114 degrees Centigrade at atmospheric pressure.

An embodiment of the invention is a method of making a material from a polysaccharide by reacting a polysaccharide with a quaternary ammonium salt to form a polysaccharide-quaternary ammonium salt complex; dissolving the polysaccharide-quaternary ammonium salt complex in an organic solvent that has a boiling point of less than 190 degree Centigrade at atmospheric pressure; and decorating the polysaccharide in the polysaccharide-quaternary ammonium salt complex with a polymerizable monomer to make a polysaccharide macromer; decorating the polysaccharide in the polysaccharide-quaternary ammonium salt complex with a polymerizable monomer to make a polysaccharide macromer. Moreover there may be included a step of polymerizing the polysaccharide macromer to make a polysaccharide polymer. There may further be included a step of polymerizing the polysaccharide macromer to form a hydrogel.

An embodiment of the invention is a material for use in a medical context, the material including a hydrogel made of a material including polymers, the polymers including heparin polymers made of polymerizable heparin macromers, the hydrogel having covalently crosslinked polymers such that the hydrogel remains intact in water. The heparin macromers may be macromers that are polymerizable while in a solution or in a suspension. The hydrogel may include polymerizable heparin macromers polymerizable in aqueous solvent and/or polymerizable heparin macromers are polymerizable in organic solvent. The amount of heparin in the heparin hydrogel may be least 1% as measured by dividing the dry weight of heparin macromers by the total dry weight of the hydrogel. And the amount of water in the heparin hydrogel may be at least 5% as measured by dividing the weight of water in the hydrogel by the total weight of the hydrated hydrogel and is preferably in the range of 10%-90% and more preferably 60%-80% water.

An embodiment of the invention is a material for use in a medical context, the material including a hydrogel made of a material including polymers, the polymers including polysaccharide polymers made of polymerizable polysaccharide macromers, the hydrogel having covalently cross-linked polymers such that the hydrogel remains intact in water, and the polysaccharide macromers being macromers that are polymerizable while in a solution or in a suspension.

An embodiment of the invention is a material for use in a medical context, the material including a hydrogel including polymers, the polymers including heparin polymers made of polymerizable heparin macromers, the hydrogel having covalently cross-linked polymers such that the hydrogel remains intact in water, the heparin macromers being heparin molecules decorated with a monomer chosen from the group consisting of monomers polymerizable by free-radical polymerization, monomers polymerizable by addition polymerization, and monomers polymerizable by condensation polymerization.

An embodiment of the invention is a material for use in a medical context, the material including a hydrogel including polymers, the polymers including polymers made of polysaccharide macromers, the hydrogel being covalently cross-linked such that the hydrogel remains intact in water, the polysaccharide macromers being polysaccharides decorated with a monomer chosen from the group consisting of monomers polymerizable by free-radical polymerization, monomers polymerizable by addition polymerization, and monomers polymerizable by condensation polymerization.

An embodiment of the invention is a vessel for use in a medical context, the vessel comprising: a tubular member with an inside wall defined by an inner diameter and an outside wall defined by an outside diameter joined by a thickness, a portion of the cylinder having its inner wall and outer wall covered with a hydrogel, the hydrogel including polymers, the polymers including heparin polymers made of polymerizable heparin macromers, with the hydrogel having covalently cross-linked polymers such that the hydrogel remains intact in water.

The hydrogel for the small diameter vascular graft and other such vessels is preferably at least several μm thick, and more preferably is at least about 50 μm thick, and even more preferably about 500-800 μm thick. The vessel's polysaccharide macromers may be polysaccharide molecules decorated with a monomer chosen from the group consisting of monomers polymerizable by free-radical polymerization, monomers polymerizable by addition polymerization, and monomers polymerizable by condensation polymerization. In contrast to certain prior art inventions, the polysaccharide macromers of the present invention may be macromers that are polymerizable while in a solution or in a suspension.

An embodiment of the invention is a vessel wherein the diameter of the minimum cross-sectional area available for blood flow through the vessel after the vessel is covered with hydrogel is less than approximately 6.0 mm. The vessel may be a fabric vessel that has pores and the hydrogel is continuous through a portion of the pores of the fabric vessel.

An embodiment of the invention is a coated stent. Another embodiment is a tissue engineering matrix. Another embodiment is a medical device covered to make a biomaterial covering around the device.

The medical device may be coated on one surface, or a portion thereof. Alternatively, the device may be completed coated on all exterior surfaces. An encapsulated device is coated on all surfaces with an essentially continuous material. If the material is a hydrogel, the hydrogel is preferably crosslinked so as to have an increased strength. A continuous hydrogel is distinguished from a thin coating because the coating is attached or adsorbed to the coated surface and is stable so long as that attachment is maintained. But a hydrogel forms a coherent structure that has stability independent of its attachment to the encapsulated surface. The term encapsulated, as used herein, means to cover. In the case of an encapsulated medical device, the covering is essentially total. In the case of a hydrogel encapsulating a tube, the inside and outside of the tube are covered. The ends of the tube are not necessarily covered.

An embodiment of the invention is a polymer (or macropolymer) of vinylpyrrolidone. Vinylpyrrolidone polymers or oligomers may be decorated with a polymerizable group using techniques known to those of ordinary skill in these arts to make a vinylpyrrolidone macromer that is polymerizable. The vinylpyrrolidone macromer may be polymerized to make a three-dimensional cross-linked structure. Or the vinylpyrrolidone macromer may be polymerized to make a larger polymer. Further, cross-links may be incorporated into the larger polymer.

This larger polymer has different properties, e.g., molecular weight, branched structure, cross-linked structure, than the unpolymerized starting material. These properties may be manipulated to achieve a polymeric vinylpyrrolidone that has superior adsorbtive properties. An unbranched, uncrosslinked polymer of vinylpyrrolidone is poorly adsorbtive. A multi-armed crosslinked or branched polymer, however, is highly adsorbtive and stable. But a polymer that is too highly crosslinked will become insoluble and will fall out of solution so that it is poorly adsorptive and difficult to use in coating techniques.

Techniques for readily determining the molecular weight of large crosslinked polymers are not available. Therefore it is usually necessary to perform routine optimization procedures to develop multi-armed polymers with appropriate branching or crosslink densities. For example, a 100,000 molecular weight vinylpyrrolidone that has been decorated with between two to ten polymerizable groups is placed into solution in five samples that vary in concentration by a factor of ten. Each sample is exposed to initiating conditions to react all of the polymerizable groups. A portion of the surface that is to be coated, e.g., a wire or tube, is exposed to the samples for a set time, preferably between about 2-10 hours. The portion is removed, rinsed in aqueous solution, and tested for adsorption. The sample that caused the highest amount of adsorption is identified and the procedure is repeated with a new concentration range built around the optimal solution. Samples wherein the polymers fall out of solution are rejected as having polymers that are too highly crosslinked. A range of parameters may be varied to ascertain the optimal conditions, including starting polymeric molecular weight, number of polymerizable groups per polymer, and solution concentrations. This optimization procedure is applicable for making polymeric, linear, high-molecular weight, and multi-armed polysaccharides as well as linear, multi-armed, and high molecular weight vinylpyrrolidones.

The vinylpyrrolidone polymer (or macropolymer) is useful for making lubricious coatings. The coatings may be made on essentially any object. The coatings may be made, for example, by drying a solution of vinylpyrrolidone polymer, multi-armed polymer, or macromer onto an object. The macromer may subsequently be polymerized. Alternatively, the object may be covered with the macromer and the macromer polymerized to make a coating or encapsulating membrane. The vinylpyrrolidone macropolymer or the macromer may be combined with other monomers/polymer/macromers, especially those described herein.

The preferred objects for coating are medical devices or components thereof. For example, springs, wires, guide wires, pacemaker leads, stents, implants, antennae, sensors, glucose sensors, tubing, blood bypass tubing, syringes, catheters, i.v. bags, needles, oxygen tubing, ventricular assist device components, and trochars.

The present invention also has inventive embodiments related to the making of the materials described herein. One aspect of making polysaccharide macromers and the like involves using organic solvent-soluble mucopolysaccharides. An aspect of this invention is that a complex of the mucopolysaccharide is formed with a cationic moiety, where the complex is organic soluble. The mucopolysaccharide part of the organic soluble complex can subsequently undergo a variety of chemical reactions. After completion of the chemical reaction, the mucopolysaccharide is de-complexed, producing a chemically modified mucopolysaccharide modified in organic solvent (O-MPSAC) that still retains its functional characteristics. As in the case of heparin, the chemically modified heparin is produced in its active anti-thrombogenic form. The macromers may be used to form the hydrogels or the linear or multi-armed polymers of the invention.

An aspect of this invention is that a mucopolysaccharide is chemically modified in water or dimethylsulfoxide (DMSO) or another equivalent solvent or solvent mixtures, herein referred to W-MPSAC. The W-MPSAC is then complexed with a cationic moiety to form a complex that is organic soluble, which can undergo further chemical reactions. The W-MPSAC may then be de-complexed.

The schemes shown in FIGS. 9 and 10, scheme I and scheme II, respectively, show these aspects of the invention. The chemical reaction in FIG. 9 can consist of chemically attaching the O-MPSAC to the surface of a material that contains reactive species. The chemical reaction in FIG. 9 can also consist of the incorporation of a functional group to the O-MPSAC that can undergo a further chemical reaction by free radical process or by photo initiated reaction or chemical coupling reaction to various polymers.

The first chemical reaction in FIG. 10 can consist of the incorporation of a functional group to the mucopolysaccharide that can undergo a further chemical reaction by free radical process or by photo initiated reaction. The first chemical reaction in FIG. 10 can also consist of chemical coupling reactions to various other chemical moieties.

The second chemical reaction in FIG. 10 can consist of chemically attaching the W-MPSAC to the surface of a material that contains reactive species. The second chemical reaction in FIG. 10 can also consist of the incorporation of a functional group to the W-MPSAC that can undergo a further chemical reaction by free radical process or by photo initiated reaction or chemical coupling reaction to various polymers.

The use of synthetic materials has gained wide-ranging acceptance in recent years as suitable materials for medical devices. The extent of their application has extended from simple disposable devices, like syringes, blood bags, catheters, also products like extracorporeal devices, artificial blood vessels, stents, stent grafts to complex artificial organs, such as kidneys, lung, liver, heart assist devices and implantable devices. These medical devices are required to have the appropriate functional properties, durability, and biological safety.

There is now emerging an additional requirement for these medical devices, especially implantable devices, to have biocompatibility with the biological environment, with minimum or no tissue rejection or reaction. Anti-thrombogenicity is a biocompatibility property that is important in many cases.

Prior art for imparting biocompatible properties to medical devices consisted of two main routes: (1) certain schemes for attaching a mucopolysaccharide (e.g., heparin) to a surface (2) chemical modification to introduce groups onto the mucopolysaccharides or the surface to make them hydrophilic, zwitterionic and/or charged, (e.g., anionic or cationic).

Route (1) has been achieved by: (I) blending or attaching an organic-soluble polymer to heparin so that the heparin goes into solution in organic solvent; (II) treating heparins to dissolve them into an organic solvent and using the organic solution to coat a medical device, (III) electrostatic binding of heparin to a surface, and (IV) chemically linking the heparin to the surface.

To cite a few examples of these methods, Pusineri et al disclose in U.S. Pat. No. 4,469,827 polymer compositions containing quarterinised amino groups that ionically bind to heparin. Hsu discloses ionic heparin coating in U.S. Pat. No. 5,047,020, where alkylbenzl ammonium cations are used to complex with heparin. U.S. Pat. No. 5,541,167, describes a coating composition consisting of stearyldimetylbenzyl ammonium heparin complex with antifoaming agents. Hsu et al in U.S. Pat. No. 5,417,969 inform processes for coating the surface of polyvinylchloride with an organic solvent soluble solution of heparin complexed with an organic cation. EP 0 769 503 A2, patent application discloses a heparin complex coating that contains stable ionic bonding and where reduction in anticoagulant activity is minimized. The preferred quaternary ion is alkyldimethylammonium. Yokota and et al have described (in EP 0 781 566), an organic soluble heparin complex coating for medical devices, where the cation consists of a quaternary phosphonium moiety. In another disclosure, U.S. Pat. No. 5,270,046, a monomer is formed containing quaternary ammonium groups, which are complexed with heparin. The monomeric complexed heparin is polymerized with other monomers. In general, however, these coatings fail under prolonged use in physiological conditions. The reason for failure is that ions generally decomplex from the heparin, causing the release of the heparin and the cation.

A preferred embodiment of the present invention is to chemically attach an O-MPSAC to the surface of a medical device that contains reactive species. The surface reactive species are able to react with the mucopolysaccharide, which is followed by decomplexation, leaving the mucopolysaccharide bound to the surface. This is exemplified by forming an organic solvent soluble heparin complex, which can be reacted with but not limited to, isocyanate or epoxide groups, which have been incorporated to the surface of the medical device. The isocyanate or epoxide groups are able to react with free hydroxyl of the heparin to form urethane or ether linkage. In another manner the isocyanate or epoxide groups are able to react with the free amino groups of the heparin to form urea or substituted amine linkage. On completion of the surface reaction the heparin is decomplexed with salt solution, leaving the heparin chemically bound to the surface in its active form. The organic soluble heparin complex can be applied to the medical device by, e.g., dip coating, spray coating or any other coating process.

Another preferred embodiment of this invention is to chemically modify the mucopolysaccharide component of the organic solvent soluble complex (see FIG. 9), to produce chemically activated O-MPSAC, which is activated to be able to undergo further chemical reactions. This is exemplified by forming an organic solvent soluble heparin complex, which can be reacted with but not limited to, isocyanatoethyl methacrylate or methacryloyl chloride. The isocyanatoethyl methacrylate or methacryloyl chloride is able to react with free hydroxyl of the heparin to form methacrylate urethane or methacrylate ester linkage with the heparin. In another manner the isocyanatoethyl methacrylate or methacryloyl chloride is able to react with the free amino groups of the heparin to form methacrylate urea or methacrylate amide linkage with the heparin. Other polymerizable groups may be substituted for methacrylates.

The complexed methacrylate heparin of the form described above can undergo free radical polymerization with other macromers and/or monomers, either in solid state, gel state, in solution, in emulsion, or in suspension. The final polymer, where the heparin complex is attached to the polymer backbone, can be used to coat medical devices. The heparin is then decomplexed with salt solution, leaving the active heparin coated onto the medical device. Other polysaccharides or proteoglycans may be substituted for heparin. And other polymerizable groups may be substituted for methacrylates.

Polymers made of polysaccharide macromers are distinct from the macromers. The polymers are made of more than one macromer. The polymers have a synthetic polymeric backbone formed by the polymerization of the polymerizable groups. The polymers have a higher molecular weight than the macromers, a factor that affects their solubility and their stability when adsorbed or otherwise attached to a surface. The polymers may have a linear, branched, or cross-linked structure. Such polymers may be distinguished from hydrogels in that a hydrogel is a solid object that is incapable of being dissolved or forming a suspension unless it is destroyed, e.g., by grinding. "Synthetic" as used herein means not naturally found in nature and does not refer to the process whereby an object is made.

The multi-armed and high molecular weight polymers have superior adsorptive properties compared to unmodified polymers. The optimal degree of branching or cross-linking that is appropriate is determinable by routine optimization processes as described for preparing lubricious surfaces. The modified polymers are placed into solution and exposed to the surface to be modified. The coating may be dried onto the coated surface.

Subsequent processing of the coatings of the invention may be used to further secure the coating to the surface. The polymers of the coating may be prepared to have polymerizable groups or functional groups that are reactive with the surface. For example, methacrylates, photopolymerizable groups, or isocyanates may be used. Alternatively, the surface may be made chemically reactive, for example by using epoxide. The chemical groups make bonds with the surface to further secure it. Polymerizable groups may be polymerized or reacted with the surface or with the other crosslinked polymers to further secure the coating on the surface.

Alternatively, the heparin macromer may be polymerized to form a three-dimensional crosslinked hydrogel. The cross linking may be accomplished by providing an average of at least two polymerizable groups per macromer or by mixing the macromers with crosslinkers that have at least two polymerizable groups.

A complexed methacrylated heparin macromer may be decomplexed with salt solution, giving a methacrylated heparin macromer that can undergo polymerization with other macromers and/or monomers, by e.g., solution, emulsion, or suspension polymerization. The final polymer, where the active heparin is attached to the polymer backbone, can be used to coat medical devices. Thus the macromers may be polymerized to form larger macromers or polymers. Or they may be polymerized to form a three-dimensional hydrogel.

Another embodiment of this invention is a chemically modified O-MPSAC which is able to undergo photochemical reactions. This is exemplified by forming an organic solvent soluble heparin complex, which can be chemically modified to contain photochemical reactive groups that are able to link to the surface of medical devices. The photochemical reactive groups can consists of allyl, vinyl, acrylates, methacrylates, azides, nitrenes, carbenes and excited states of ketones, diazo, azo compounds and peroxy compounds, and such groups as are cited in and those cited in WO 90/00887, which is hereby incorporated herein by reference. An advantage of this method is that photochemical reactive groups may be bound to the heparin complex in organic solvents, and the resultant product may then be dissolved in organic solvent and coated onto the medical device. Then applying the appropriate electromagnetic radiation to carry out the photochemical reaction; this is followed by decomplexation, leaving the active heparin bound to the surface.

An advantage of the modified polymers and the polysaccharide macromers of the invention is that they may be reacted with a surface while in solution. For example, modified polymers with polymerizable groups may be polymerized while in solution. Or photoactivatable groups or electrophilic groups may be activated while the polymer or macromer is in solution. These approaches are particularly effective when organic solvents are used because many chemical reactions are much more efficient in organic solvents as compared to aqueous solvents, e.g., electrophile-nucleophile reactions. The present disclosure provides numerous techniques for bringing polysaccharides and modified polymers into solution so that an effective reaction with the surface may be performed.

Another preferred embodiment of the invention comprises of the chemical modification of the mucopolysaccharide in water or dimethyl sulphoxide or another equivalent solvent or solvent mixtures. This is exemplified by the reaction of the activated imidazole carbonate of polyethyleneglycol methacrylate (see WO 97/41164, hereby incorporated by reference herein) with heparin to form the heparin-polyethyleneglycol methacrylate. The heparin-polyethyleneglycol methacrylate is then complexed (W-MPSAC, Scheme 2). The W-MPSAC can then undergo further chemical reaction in an organic solvent, e.g., by free radical process or by photo initiated reaction. Alternatively, the heparin-polyethyleneglycol methacrylate can undergo chemical reactions by free radical process or by photo initiated reaction without the complexation step. The resultant product may then be complexed to form an organic soluble heparin complex.

EXAMPLE 1

Heparin Complex 5 g sodium heparin (Celsus Laboratories, Inc, USP lyophilized from porcine intestinal mucosa) was dissolved in 80 ml de-ionized water and allowed to stir for 1 hour in a 250 ml beaker.

8 g benzalkonium chloride (Aldrich Chemical Company, Inc) was allowed to dissolve in 80 ml de-ionized water with gentle warming (40-50° C.) on a magnetic stirrer hotplate for 1 hour and then allowed to reach room temperature.

To the above vigorously stirred solution of sodium heparin, the benzalkonium chloride solution was added. A white precipitate immediately formed and the suspension was further stirred for 1 minute. The precipitate was filtered through a Whatman qualitative filter paper (grade 1).

The white precipitate was collected from the filter paper and re-suspended in 400 ml deionized water and allowed to stir for 20 minutes. The suspension was filtered as above and resuspended in 400 ml de-ionized water and filtered again. The precipitate was once again suspended in 400 ml de-ionized water and then poured into a dialysis membrane Cellu Sep:MWCO 3,500 and dialyzed against 10 L de-ionized water for a minimum of 16 hours.

The precipitate was collected and dried on a glass dish in a vacuum oven at 60° C. for 12 hours.

Dry gray-yellow crystals were obtained with a yield of 10 g.

EXAMPLE 2

3 g 4,4'-methylenebis (phenyl isocyanate) (MDI) (Aldrich Chemical Company, Inc) was dissolved in 100 ml anhydrous tetrahydrofuran (THF). Polyurethane tubing was dipped in to the above solution for 30 seconds and was then allowed to stir-dry at 60° C. for 1 hour.

5 g of dry crystals of complexed heparin from Example 1 were dissolved in 100 ml anhydrous dichloromethane (DCM). The MDI coated polyurethane tubing was dipped into the DCM solution of complexed heparin for 30 seconds and then allowed to air-dry for 2 hours.

The tubing was dyed with 0.075% w/v pH 8.5 toludine blue aqueous solution for 30 seconds and washed with de-ionized water. A very faint purple color due to the complexed heparin was observed. The tubing was then immersed in 25% w/v solution of sodium chloride at 40° C. for 30 minutes. The tubing was washed with de-ionized water and again dyed. An intense dark purple color due to complexed heparin was observed.

In a similar experiment where the polyurethane tubing was not initially coated with MDI and was de-complexed in sodium chloride solution (as above) no purple coloration due to the heparin was observed.

EXAMPLE 3

1. Heparin Methacrylate (Methacryloyl Chloride)

5 g of dry crystals of complexed heparin from Example 1 were dissolved in 100 ml anhydrous DCM in a 250 ml quickfit conical flask. To this was added 0.1265 g ($1.25\times10^{-3}$ moles) triethylamine.

Methacryloyl chloride (Aldrich Chemical Company, Inc) was distilled under reduced pressure to obtain a very pure sample. 0.1306 g ($1.25\times10^{-3}$ moles) of the above distilled methacryloyl chloride was dissolved in 30 ml anhydrous DCM and placed in a stoppered quickfit pressure equalizing funnel above the vigorously stirred solution of DCM containing the complexed heparin. The methacryloyl chloride solution was added drop-wise over a period of 30 minutes to the complexed heparin solution in DCM.

The DCM was rotary evaporated and the complexed heparin methacrylate was dried in a vacuum oven at 40° C. for 2 hours.

Complexed methacrylate was characterized by $^{1}$H and $^{13}$C.

0.2 g of the above complexed heparin methacrylate was dissolved in 10 ml 2-hydroxyethylmethacrylate and to this was added 0.02 g ethylene gluol dimethacrylate and 0.02 g 2,2'-azobis (2,4-dimethylvaleronitrile) (Dupont). The above clear solution was degassed for 30 minutes.

The above polymerization mixture was poured into a polypropylene concave mold and then a polypropylene convex mold was placed onto the concave mold allowing the excess solution to overflow, thereby uniformly filling the space between the concave and convex molds. The sealed molds were then heated to a temperature of 65° C. for 4 hours and then at 110° C. for 1 hour.

The molds were cooled and opened to obtain a clear dehydrated rigid hydrogel. These were then hydrated in de-ionized water for 10 hours, after which they were placed in boiling solution of 25% w/v sodium chloride aqueous solution for 1 hour and then equilibrated in deionized water. The hydrogel was dyed (as in Example 2) and a uniform intense dark purple coloration was observed throughout the hydrogel.

In a similar experiment where no methacrylate of the heparin was formed, a hydrogel of the complexed heparin alone was formed. After boiling in 25% w/v sodium chloride aqueous solution and equilibrating in water the hydrogel was dyed. Dark purple precipitated particles of heparin could be observed on the surface of the hydrogel and were easily washed away with deionized water, leaving a blue coloration to the hydrogel. This coloration is identical to the hydrogels formed without any complexed heparin.

2. Heparin Methacrylate (Isocyanatoethylmethacrylate)

5 g of dry crystals of complexed heparin from Example 1 were dissolved in 100 ml anhydrous DCM in a 250 ml thick-walled glass bottle with cap. To this was added 0.194 g (1.25×

$10^{-3}$ moles) 2-isocyanatoethylmethacrylate (Aldrich Chemical Company, Inc) and 0.05 g dibutyltin dilaurate (Aldrich Chemical Company, Inc). The cap was screwed on tight and the solution was stirred for 16 hours at 40° C.

The DCM was rotary-evaporated off and the product dried in a vacuum at 40° C. for 2 hours.

As in Example 3(1), hydrogels were made and the heparin was decomplexed and dyed. Again, a uniform intense dark purple coloration was observed throughout the hydrogel whereas the complexed heparin with no methacrylate coupling heparin particles precipitated on the surface of the hydrogel and were easily washed away with de-ionized water.

EXAMPLE 4

5 g of Heparin methacrylate from example 3 i) was dissolved in 100 ml of 2-propanol. To this was added 20 g methoxypolyethlyeneglycol 2000 methacrylate (MPEG 2000 MA) (Inspec U.K.) and 3 g of 2-hydroxyethylmethacrylate.

A 250 ml, 3-necked reaction vessel equipped with stirrer, thermometer, condenser and nitrogen inlet tube was charged with 100 ml 2-propanol. To the 2-propanol was added 5 g of heparin methacrylate [from example 3(i)], 20 g methoxypolyethyleneglycol 2000 methacrylate (MPEG 2000 MA) (Inspec U.K.) and 3 g 2-hydroxyethylmethoxylate. (HEMA) The 250 ml, 3 necked reaction vessel was placed in a silicone oil bath at 120° C. and the 2-propanol was stirred gently and nitrogen was bubbled through the solution (100 $cm^3$/min).

When the temperature in the 250 ml, 3-necked reaction vessel reached 75° C., 0.25 g 2,2'-azobis (2,4-dimethylvaleronitrile) was added and the stirrer speed was increased to 750 rpm. After approximately 15 minutes a very viscous solution was obtained and the reaction was allowed to continue for 30 minutes, periodically added 30 ml 2-proponal to dilute and reduce the viscosity of the solution. In total four 30 ml aliquots of 2-propanol was added.

The polymer was cooled down to room temperature and the isopropanol rotary evaporated off and the polymer dried in a vacuum oven at 40° C. for 8 hours.

GPC (Gel permeation chromatography) showed that the average molecular weight of the polymer was approximately 400,000 when using polyethylene glycols as standards.

EXAMPLE 5

3 g MDI was dissolved in 100 ml of anhydrous THF. A 150 mm long and 2 mm diameter polyurethane tube was dipped into the above solution for 30 seconds and was then allowed to air dry at 60° C. for 1 hour.

5 g of heparin copolymer from Example 4 was dissolved in anhydrous DCM. The MDI coated polyurethane tubing was dipped into the DCM solution of copolymer for 30 seconds and was then allowed to air at 60° C. for 30 minutes and then at room temperature for 16 hours.

The tubing was immersed in 25% w/v sodium chloride solution at 40° C. for 30 minutes. The tubing was washed with de-ionized water and dried with toludine blue (example 2). A homogenous intense dark purple coloration was obtained on the tubing. In addition the polyurethane tubing was completely wetted and very lubricious. The lubricity did not diminish even when it was rubbed between forefingers and thumb 20 times. The tubing was then immersed in phosphate buffered saline at 50° C. for 16 hrs and then rubbed between the forefinger and thumb. Again there was no observable discharges in lubricity.

EXAMPLE 6

As in Example 4, 5 g heparin methacrylate was copolymerized, except that instead of MPEG 2000 MA and HEMA, 20 g N-vinylpyrrolidone was used as the co-monomer in 2-propanol. The polymerization was allowed to continue for 1 hour.

The average molecular weight of the copolymer was approximately 300,000 as determined by GPC.

As in Example 5 a 150 mm long and 2 mm diameter polyurethane tubing was dipped into a 3% w/v MDI in THF solution and air dried at 60° C. for 1 hour.

The tubing was then dipped in a 5% w/v heparin-vinylpyrrolidone copolymer in DCM for 30 seconds and then air dried at 60° C. for 2 hours.

The tubing was then immersed in 25% w/v sodium chloride solution at 40° C. for 30 minutes. The tubing was washed with de-ionized water and dyed with toludine blue. A homogenous intense dark purple colorization was obtained. The polyurethane tubing was completely wetted and extremely lubricious. The lubricity was equivalent to that obtained for in Example 5.

EXAMPLE 7

5 g heparin methacrylate was copolymerized with 20 g acrylic acid in 2-proponal. The reaction conditions were the same as in Example 6.

The average molecular weight was determined to be 400,000 using GPC and polyacrylic acids as standards.

As in Example 5 a 150 mm long and 2 mm diameter polyurethane tubing was dipped into a 3% w/v MDI in THF solution and air dried at 60° C. for 1 hour.

The tubing was dipped into a 5% w/v heparin-acrylic acid copolymer in methanol/dimethylacetamide solution (90:10) for 30 seconds and the air dried at 60° C. for 3 hours.

The lubricity of the surface of the polyurethane tubing was very similar to that in Example 5 and 6 after washing in 25% w/v sodium chloride solution (as performed in Example 5 and 6).

XPS confirmed the presence of heparin on the surface as $SO_4$ groups be detached on the surface of the polyurethane tubing.

EXAMPLE 8

PVC tubing 150 mm long 2 mm in diameter were coated with the heparin copolymers synthesized in Example 4, 6 and 7. The coating conditions for the respective heparin copolymers were identical to the Examples 5, 6 and 7 respectively.

In all cases a very durable lubricious coating (when wet) was obtained and the presence of heparin on the surface of the PVC was detected either using toludine blue or XPS.

EXAMPLE 9

A polyurethane tube (150 mm long, 2 mm diameter) was dipped into a 2% w/v solution of poly [1,4-phenylenediisocyanate-co-poly (1,4-butanediol)]diisocyanate (Aldrich Chemical Co.) in anhydrous THF and allowed to air dry at 60° C. for 2 hours.

2 g of heparin complex (from Example 1), 2 g polyethylene oxide (M.W. 100,00) (Aldrich Chemical Co.) and 0.25 g MDI were dissolved in 100 ml anhydrous DCM. The polyurethane tubing was dipped with the above solution for 30 seconds and allowed to air dry at 60° C. for 1 hour and then at 22° C. for 16 hours.

The polyurethane tubing was immersed in 25% w/v sodium chloride solution at 40° C. for 30 minutes and then washed with de-ionized water and then dyed with toludine blue. An intense homogenous dark purple color developed on the tubing and when wet the tubing was highly lubricious. The lubricity was comparable to in Example 5, 6 and 7.

EXAMPLE 10

A similar experiment to the one in Example 9 was conducted with polyvinylpyrrolidone (M.W. 1,300,000) (Aldrich Chemical Co.) with all the experimental conditions the same. Again the results showed that heparin was present on the surface and the polyurethane tubing was highly lubricious and comparable to the coating in Example 9.

EXAMPLE 11

A PTFE tube measuring 3.8 mm O.D; length 8 cm was placed on a rotatable mandrel. Placed over the PTFE was a knitted fabric tube measuring 4.0 mm I.D; length of 7 cm.

A methacrylated polyvinylpyrrolidone (MPVP) was made by dissolving 6 g of polyvinylpyrrolidone (PVP) in dichloromethane. A solution of isocyanato ethyl methacrylate (0.8 g dissolved in 20 ml of dichloromethane) was added drop wise to the stirred solution of PVP. The reaction was allowed to proceed for a further 2 hours. Dichloromethane was then rotary evaporated and the MPVP formed was used in the vascular graft formulation as per the following: Hydoxyethyl Methacrylate 18 g; Heparin Methacrylate (as from example 3) 1 g; MPVP 0.6 g; Ethylene glycol dimethacrylate 0.08 g; thermal initiator 0.12 g (Vazo 52).

The vascular graft formulation was then added drop wise onto the rotating knitted fabric until a homogeneous viscous film was formed, which totally encapsulated the fabric. Then the graft was exposed to UV light from a medium pressure mercury arch lamp for 10 minutes; then the graft was placed in a vacuum oven for 3 hours at 70° C.

The heparin contained in the graft was de-complexed with saturated NaCl solution. The final vascular graft had a hydrogel that totally encapsulated the fabric, which had a water content of 50%. Heparin activity was measured by antithrombin binding assay and was found to be 5 units per 100 $mm^2$.

EXAMPLE 12

This example shows that vascular grafts made as described herein are effective for use with patients. A 28 day animal study was carried out on two pigs. The vascular grafts as made according to Example 11 were implanted in the carotid artery of each animal using aseptic surgical techniques known to those skilled in the art. The carotid arties were visualized at day nine, and day 28 using a medical X-ray arteriogram. The arteriogram showed that the grafts were patent with endothelial cells, were clean, and showed no evidence of thrombus at both days.

The embodiments of the invention set forth herein are exemplary and not intended to be limiting in scope. Patents, patent applications, and articles mentioned in this application are hereby incorporated herein by reference.

The invention claimed is:

1. A medical apparatus shaped as a tubular member and comprising:

a three-dimensional crosslinked hydrogel made by a process that comprises polymerizing, in organic solvent, water-insoluble quaternary ammonium-polyanionic polysaccharide macromer salt complexes that comprise covalently attached vinylic monomers that undergo the polymerizing to form polymers crosslinked to form the hydrogel, with the hydrogel forming a tubular member having a free exterior surface and a free interior surface connected by a thickness of the crosslinked hydrogel, wherein said vinylic monomers are joined through covalent bonds to the polysaccharide in the polysaccharide macromer salt complexes.

2. The medical apparatus of claim 1 wherein the vinylic monomers are members of the group consisting of hydroxyethylmethylacrylates, methyl methacrylates, methacrylates, acrylates, photopolymerizable monomers, vinylic monomers with hydroxyl groups, vinylic monomers with glycerol groups, vinylic monomers with polyoxyalkylene ether groups, vinylic monomers with polypropylene oxide groups, monomers with vinyl groups, vinylic monomers with zwitterionic groups, vinylic monomers with silicone groups, vinylic monomers having sulphate groups, and vinylic monomers having sulphonate groups.

3. The medical apparatus of claim 1 wherein the polysaccharide macromers include at least one macromer chosen from the group consisting of macromers of glycosaminoglycans, hyaluronic acid, chondroitin sulfate, dermatan sulfate, heparan sulfate, keratan sulfate, and proteoglycans.

4. The medical apparatus of claim 1 wherein the polysaccharide macromers before polymerization comprise at least two of the covalently attached vinylic monomers.

5. The medical apparatus of claim 1 wherein the hydrogel comprises at least one polymerized vinylic monomer chosen from the group consisting of polyhydroxyethylmethylacrylates, methyl methacrylates, methacrylates, acrylates, photopolymerizable monomers, monomers with hydroxyl groups, monomers with glycerol groups, monomers with polyoxyalkylene ether groups, monomers with polypropylene oxide groups, monomers with vinyl groups, monomers with zwitterionic groups, monomers with silicone groups, monomers having sulphate groups, and monomers having sulphonate groups.

6. The medical apparatus of claim 1 wherein the hydrogel comprises at least about 5% polysaccharide by weight when dehydrated.

7. The medical apparatus of claim 1 wherein the tubular member further comprises a tube of a non-hydrogel material encapsulated between the interior surface and the exterior surface.

8. The medical apparatus of claim 7 wherein the tube is a stent.

9. The medical apparatus of claim 7 wherein the tube is a vascular graft or an implantable tubular member.

10. The medical apparatus of claim 7 wherein the non-hydrogel tube comprises a material chosen from the group consisting of silicone polymer, woven fabric, knitted fabric, polyester, polyamide, fluorocarbon, polyethylene, polycarbonate, polyurethane, and polystyrene.

11. The medical apparatus of claim 10 further comprising an impermeable barrier between the non-hydrogel tube and the interior surface, wherein the barrier is encapsulated by the hydrogel.

12. The medical apparatus of claim 10 further comprising a permeable barrier between the non-hydrogel tube and the interior surface, wherein the barrier is encapsulated by the hydrogel.

13. The medical apparatus of claim 1 wherein the tubular member has a central lumen that has a diameter of less than about 6 mm.

14. The medical apparatus of claim 1 wherein the exterior surface is free of any materials covalently bonded thereto.

15. The medical apparatus of claim 1, wherein the exterior surface is free of covalent or ionic bonds to another material.

16. The medical apparatus of claim 15 wherein the polysaccharide macromers before polymerization comprise at least one vinylic monomer chosen from the set consisting of hydroxyethylmethylacrylates, methyl methacrylates, methacrylates, acrylates, vinylic monomers with hydroxyl groups, vinylic monomers with glycerol groups, vinylic monomers with polyoxyalkylene ether groups, vinylic monomers with polypropylene oxide groups, monomers with vinyl groups, monomers with zwitterionic groups, vinylic monomers with silicone groups, monomers having sulphate groups, and vinylic monomers having sulphonate groups.

17. The medical apparatus of claim 15 wherein the hydrogel further comprises at least one polymerized monomer chosen from the group consisting of hydroxyethylmethylacrylates, methyl methacrylates, methacrylates, acrylates, photopolymerizable monomers, monomers with hydroxyl groups, monomers with glycerol groups, monomers with polyoxyalkylene ether groups, monomers with polypropylene oxide groups, monomers with vinyl groups, monomers with zwitterionic groups, monomers with silicone groups, and monomers having sulphate groups.

18. The medical apparatus of claim 15 wherein the hydrogel comprises at least about 5% heparin by weight when dehydrated.

19. The medical apparatus of claim 15 wherein the tubular member further comprises a tube of a non-hydrogel material encapsulated therein.

20. The medical apparatus of claim 19 wherein the tube comprises a material chosen from the group consisting of silicone polymer, woven fabric, knitted fabric, polyester, polyamide, fluorocarbon, polyethylene, polycarbonate, polyurethane, and polystyrene.

21. The medical apparatus of claim 19 wherein the tubular member has a lumen with a diameter of less than about 6 mm.

22. The medical apparatus of claim 1 wherein the polysaccharide comprises heparin.

23. A biocompatible encapsulation for a medical device comprising a plurality of water-insoluble quaternary ammonium-polyanionic polysaccharide macromer salt complexes that comprise covalently attached vinylic monomers polymerized into a three-dimensional crosslinked hydrogel that encapsulates the medical device, wherein said vinylic monomers are joined through covalent bonds to the polysaccharide in the polysaccharide macromer salt complexes.

24. The encapsulation of claim 23 wherein the vinylic monomers are members of the group consisting of hydroxyethylmethylacrylates, methyl methacrylates, methacrylates, acrylates, monomers with hydroxyl groups, vinylic monomers with glycerol groups, vinylic monomers with polyoxyalkylene ether groups, vinylic monomers with polypropylene oxide groups, monomers with vinyl groups, vinylic monomers with zwitterionic groups, vinylic monomers with silicone groups, vinylic monomers having sulphate groups, and vinylic monomers having sulphonate groups.

25. The encapsulation of claim 23 wherein the polysaccharide macromers include at least one macromer chosen from the group consisting of macromers of glycosaminoglycans, hyaluronic acid, chondroitin sulfate, dermatan sulfate, heparan sulfate, keratan sulfate, and proteoglycans.

26. The encapsulation of claim 23 wherein the hydrogel further comprises at least one polymerized monomer chosen from the group consisting of polyhydroxyethylmethylacrylates, methyl methacrylates, methacrylates, acrylates, photopolymerizable monomers, monomers with hydroxyl groups, monomers with glycerol groups, monomers with polyoxyalkylene ether groups, monomers with polypropylene oxide groups, monomers with vinyl groups, monomers with zwitterionic groups, monomers with silicone groups, monomers having sulphate groups, and monomers having sulphonate groups.

27. The encapsulation of claim 23 wherein the polysaccharide comprises heparin.

28. A medical device for use with a blood vessel comprising:

- a tubular member having an interior surface that defines a lumen, an exterior surface, a porous layer, and a crosslinked hydrogel layer,
- with the crosslinked hydrogel layer made by a process comprising polymerizing, in organic solvent, a plurality of water-insoluble polymerized quaternary ammonium-polyanionic polysaccharide macromer salt complexes that comprise covalently attached vinylic monomers that undergo the polymerizing to form the hydrogel,
- with the porous layer having an exterior side and a luminal side and comprising a plurality of interstitial spaces, and
- the hydrogel layer being disposed on at least the luminal side of the porous layer, wherein said vinylic monomers are joined through covalent bonds to the polysaccharide in the polysaccharide macromer salt complexes.

29. The medical device of claim 28 wherein the porous layer comprises a fabric material containing a plurality of fabric strands and the hydrogel layer conforms to the strands.

30. The medical device of claim 28 wherein the porous layer comprises a wire mesh containing a plurality of wire strands and the hydrogel layer conforms to the strands.

31. The medical apparatus of claim 28 wherein the polysaccharide macromers before polymerization comprise at least one polymerizable vinylic monomer chosen from the set consisting of hydroxyethylmethylacrylates, methyl methacrylates, methacrylates, acrylates, vinylic monomers with hydroxyl groups, vinylic monomers with glycerol groups, vinylic monomers with polyoxyalkylene ether groups, vinylic monomers with polypropylene oxide groups, monomers with vinyl groups, vinylic monomers with zwitterionic groups, vinylic monomers with silicone groups, and vinylic monomers having sulphate groups, and vinylic monomers having sulphonate groups.

32. The medical apparatus of claim 28 wherein the polysaccharide macromers include at least one macromer chosen from the group consisting of macromers of glycosaminoglycans, hyaluronic acid, chondroitin sulfate, dermatan sulfate, heparan sulfate, keratan sulfate, and proteoglycans.

33. The medical apparatus of claim 28 wherein the polysaccharide macromers before polymerization comprise at least two polymerizable groups.

34. The medical apparatus of claim 28 wherein the hydrogel further comprises at least one polymerized monomer chosen from the group consisting of hydroxyethylmethylacrylates, methyl methacrylates, methacrylates, acrylates, photopolymerizable monomers, monomers with hydroxyl groups, monomers with glycerol groups, monomers with polyoxyalkylene ether groups, monomers with polypropylene oxide groups, monomers with vinyl groups, monomers with zwitterionic groups, monomers with silicone groups, monomers having sulphate groups, and monomers having sulphonate groups.

35. The medical apparatus of claim 28 wherein the hydrogel comprises at least about 5% polysaccharide by weight when dehydrated.

36. The medical apparatus of claim 28 wherein the tubular member has a central lumen that has a diameter of less than about 6 mm.

37. The medical apparatus of claim 28 wherein the exterior surface is free of any materials covalently bonded thereto.

38. The medical apparatus of claim 28 wherein the tube is a stent.

39. The medical apparatus of claim 28 wherein the tube is a vascular graft or an implantable tubular member.

40. The medical apparatus of claim 28 wherein the polysaccharide comprises heparin.

41. A medical device for use as a blood vessel comprising:

a tubular member with an exterior surface and a luminal surface and comprising a fabric layer and a crosslinked hydrogel coating, wherein the coating is made by a process comprising polymerizing a plurality of water-insoluble polymerized quaternary ammonium-polyanionic polysaccharide macromer salt complexes that comprise covalently attached vinylic monomers that undergo the polymerizing to form the hydrogel, wherein said vinylic monomers are joined through covalent bonds to the polysaccharide in the polysaccharide macromer salt complexes, with the fabric layer having a plurality of fabric strands and a plurality of interstitial spaces, and the hydrogel layer being disposed on at least a luminal side of the fabric layer and conforming to the strands without completely filling the interstitial spaces between the strands.

42. The medical device of claim 41 wherein the hydrogel layer comprises at least about 5% polysaccharide by weight when dehydrated.

43. The medical device of claim 41 further comprising a polymeric material disposed between the fabric and the hydrogel layer, with the hydrogel layer being in contact with the polymeric material.

44. The medical apparatus of claim 41 wherein the polysaccharide macromers before polymerization comprise at least one polymerizable vinylic monomer chosen from the set consisting of hydroxyethylmethylacrylates, methyl methacrylates, methacrylates, acrylates, vinylic monomers with hydroxyl groups, vinylic monomers with glycerol groups, vinylic monomers with polyoxyalkylene ether groups, vinylic monomers with polypropylene oxide groups, monomers with vinyl groups, vinylic monomers with zwitterionic groups, vinylic monomers with silicone groups, vinylic monomers having sulphate groups, and vinylic monomers having sulphonate groups.

45. The medical apparatus of claim 41 wherein the polysaccharide macromers include at least one macromer chosen from the group consisting of macromers of glycosaminoglycans, hyaluronic acid, chondroitin sulfate, dermatan sulfate, heparan sulfate, keratan sulfate, and proteoglycans.

46. The medical apparatus of claim 41 wherein the polysaccharide macromers include polysaccharide macromers having at least two polymerizable groups.

47. The medical apparatus of claim 41 wherein the hydrogel further comprises at least one polymerized monomer chosen from the group consisting of hydroxyethylmethylacrylates, methyl methacrylates, methacrylates, acrylates, photopolymerizable monomers, monomers with hydroxyl groups, monomers with glycerol groups, monomers with polyoxyalkylene ether groups, monomers with polypropylene oxide groups, monomers with vinyl groups, monomers with zwitterionic groups, monomers with silicone groups, monomers having sulphate groups, and monomers having sulphonate groups.

48. The medical apparatus of claim 41 wherein the tubular member has a central lumen that has a diameter of less than about 6 mm.

49. The medical apparatus of claim 41 wherein the tubular member further contains an exterior surface that is free of any materials covalently bonded thereto.

50. The medical apparatus of claim 41 wherein the polysaccharide comprises heparin.

* * * * *